(12) United States Patent
Kawabe et al.

(10) Patent No.: US 6,297,372 B1
(45) Date of Patent: Oct. 2, 2001

(54) PROCESS FOR THE PREPARATION OF HEXANITROHEXAAZAISOWURTZITANES

(75) Inventors: Shuji Kawabe; Hiroshi Miya, both of Oita; Tamotsu Kodama; Nobuhisa Miyake, both of Kurashiki, all of (JP)

(73) Assignee: Asahi Kasei Kabushiki Kaisha (JP)

( * ) Notice: Subject to any disclaimer, the term of this patent is extended or adjusted under 35 U.S.C. 154(b) by 0 days.

(21) Appl. No.: 09/242,019

(22) PCT Filed: Aug. 6, 1997

(86) PCT No.: PCT/JP97/02732

§ 371 Date: Sep. 30, 1999

§ 102(e) Date: Sep. 30, 1999

(87) PCT Pub. No.: WO98/05666

PCT Pub. Date: Feb. 12, 1998

(30) Foreign Application Priority Data

Aug. 7, 1996 (JP) .................................................. 8-223237
Aug. 7, 1996 (JP) .................................................. 8-223238
Aug. 7, 1996 (JP) .................................................. 8-223239

(51) Int. Cl.$^7$ ......................... C07D 487/22; C06B 25/34; C07B 43/02
(52) U.S. Cl. ........................................... 540/554; 540/556
(58) Field of Search .................................... 540/554, 556

(56) References Cited

U.S. PATENT DOCUMENTS 4,921,970 * 5/1990 Odie ...................................... 548/480
5,693,794   12/1997 Nielsen ................................ 540/554

FOREIGN PATENT DOCUMENTS

0753519-A1 * 1/1997 (EP) .
WO-96/23792 * 8/1996 (WO) .

OTHER PUBLICATIONS

Anthony J. Bellamy "Reductive Debenzylation of Hexabenzylhexaazaisowurtzitane" Tetrahedron vol. 51, No. 16, Apr. 1995, pp. 4711–4722.

* cited by examiner

Primary Examiner—Mukund J. Shah
Assistant Examiner—Steven M. Reid

(74) Attorney, Agent, or Firm—Finnegan, Henderson, Farabow, Garrett & Dunner, L.L.P.

(57) ABSTRACT

A nitro group-containing hexaazaisowurtzitane derivative represented by the following general formula (I):

$$W A_n N_{(6-n)} \tag{I}$$

wherein n is an integer of 4 or 5, A is an acyl group having 1–10 carbon atoms with each acyl group being the same as or different from one or more of the others, N is a nitro group and W is a hexavalent hexaazaisowurtzitane residue represented by the following formula (II):

$$\tag{II}$$

a nitroso group-containing hexaazaisowurtzitane derivative represented by the following general formula (III):

$$W A_n NS_{(6-n)} \tag{III}$$

wherein n is an integer of 4 or 5, A is an acyl group having 1–10 carbon atoms with each acyl group being the same as or different from one or more of the others, NS is a nitroso group and W is a hexavalent hexaazaisowurtzitane residue of formula (II) above, and an acyl group-containing hexaazaisowurtzitane derivative represented by the following general formula (IV):

$$W A_m H_{(6-m)} \tag{IV}$$

wherein N is an integer of 4–6, A is an acyl group having 1–10 carbon atoms with each acyl group being the same as or different from one or more of the others, H is a hydrogen atom and W is a hexavalent hexaazaisowurtzitane residue of formula (II) above, and process for preparing hexanitrohexaazaisowurtzitane represented by the following formula (VI):

$$W N_6 \tag{VI}$$

wherein N is a nitro group and W is a hexavalent hexaazaisowurtzitane residue of formula (II) above, by nitrating one of said derivatives with a nitrating agent.

17 Claims, No Drawings

PROCESS FOR THE PREPARATION OF HEXANITROHEXAAZAISOWURTZITANES

This is an application under 35 U.S.C. 371 of PCT/JP97/02732 filed Aug. 6, 1997.

TECHNICAL FIELD

The present invention relates to hexanitrohexaazaisowurtzitane and a process for preparing the same.

BACKGROUND ART

As compounds having hexaazaisowurtzitane skeletons, various arylmethyl group-containing hexaazaisowurtzitane derivatives are known which are obtained by condensation of arylmethylamines and glyoxal (J. Org. Chem., vol. 55, 1,459–1,466, 1990). Tetraacetyldibenzylhexaazaisowurtzitane is known as an acyl group-containing hexaazaisowurtzitane compound and is reported to be a precursor of hexanitrohexaazaisowurtzitane which is a material for explosives (The Militarily Critical Technologies List, Office of the Under Secretary of Defense for Acquisition, 12–22, October 1992 and Tetrahedron, Vol. 51, No. 16, 4711–4722, 1995). Further, there are known ethyl group-containing hexaazaisowurtzitane derivatives such as tetraacetyl-diethylhexaazaisowurtzitane and the like (Tetrahedron, Vol. 51, No. 16, 4711–4722, 1995) and there are also known trimethylsilylethyloxycarbonyl group-containing hexaazaisowurtzitane derivatives (JP-A-6-321962). There are known benzyl and/or ethyl group-containing hexaazaisowurtzitane derivatives other than the above-mentioned tetraacetyldibenzylhexaazaisowurtzitane, tetraacetyldiethylhexaazaisowurtzitane.

The above-mentioned hexaazaisowurtzitane derivatives having acyl groups easily substitutable with nitro groups are useful as precursors of polynitrohexaazaisowurtzitane derivatives for high-performance explosives; however, use of the above-mentioned derivatives as precursors of the nitro compounds has problems. For example, since by-products such as nitrated aromatic compounds are produced in nitration of the benzyl group-containing hexaazaisowurtzitane derivatives, it is complicated to isolate and purify therefrom hexanitrohexaazaisowurtzitane, the target compound of the present invention. On the other hand, hydrochloric acid, i.e., a strong acid, which is produced during preparation of trimethylsilylethyloxycarbonyl group-containing hexaazaisowurtzitaines, causes the decomposition of hexabenzylhexaazaisowurtzitane that is the starting material in the process. It is reported that hexanitrohexaazaisowurtzitane is obtained by nitration of the tetraacetyldibenzylhexaazaisowurtzitane, but no detailed description is found on its method of preparation (Tetrahedron, vol. 51, No. 16, 4,711–4,722, 1995). It is further reported to be difficult to prepare hexanitrohexaazaisowurtzitane by nitration of tetraacetyldiethylhexaazaisowurtzitane (Tetrahedron, vol. 51, No. 16, 4,711–4,722, 1995).

Therefore, it has been long desired to develop a process for preparing hexanitrohexaazaisowurtzitane in a high yield by use of an acyl group-containing hexaazaisowurtzitane derivative. It is also an object of the present invention to prepare hexanitrohexaazaisowurtzitane in a high yield by use of hexaazaisowurtzitane derivatives.

DISCLOSURE OF THE INVENTION

The inventors have achieved these and other objects according to these and other objects according to the present invention, which comprises the discovery of a commercially advantageous process for preparing hexanitrohexaazaisowurtzitane.

The present invention provides a nitro group-containing hexaazaisowurtzitane derivative and a process for preparing said derivative, which is represented by the following general formula (I):

   (I)

wherein n is an integer of 4 or 5, A is an acyl group having 1–10 carbon atoms with each acyl group being the same as or different from one or more of the others, N is a nitro group and W is a hexavalent hexaazaisowurtzitane residue represented by the following formula (II):

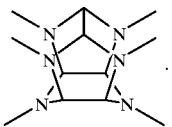   (II)

Further, the present invention provides a nitroso group-containing hexaazaisowurtzitane derivative and a process for preparing said derivative, which is represented by the following general formula (III):

   (III)

wherein n is an integer of 4 or 5, A is an acyl group having 1–10 carbon atoms with each acyl group being the same as or different from one or more of the others, NS is a nitroso group and W is a hexavalent hexaazaisowurtzitane residue represented by the following formula (II):

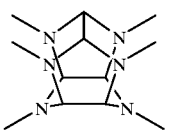   (II)

Any acyl group may be acceptable as acyl group A in the above formulae (I) and (III) so long as it has 1 to 10 carbon atoms. As acyl group A, there may be acetyl, formyl, propionyl, butyryl, isobutyryl, valeryl, hexanoyl, 2-phenylacetyl or the like. Preferably, A may be acyl groups having 1–5 carbon atoms such as formyl, acetyl, propionyl, butyryl, valeryl and the like and more preferably, A may be acyl groups having 2–4 carbon atoms such as acetyl, propionyl, butyryl and the like. In the above formulae (I) and (III), each of the n acyl groups may be the same as or different from one or more of the others.

Each of the hexaazaisowurtzitane derivatives may take the form of any of various isomers differing in the positions of acyl, nitro and nitroso groups thereof; however, any of such isomers may be used in accordance with the present invention.

Hereinbelow, descriptions will be given of methods for preparing hexaazaisowurtzitane derivatives represented by formulae (I) and (III).

The nitro group-containing hexaazaisowurtzitane derivative of general formula (I), from which hexanitrohexaazaisowurtzitane is prepared, may be prepared by nitration of W $A_m H_{(6-m)}$ as shown in the following reaction formula (1):

   (1)

wherein m is an integer of 4–6, n is integer of 4 or 5, A is an acyl group having 1–10 carbon atoms with each acyl group being the same as or different from one of more of the others, H is a hydrogen atom, N is a nitro group and W is a hexavalent hexaazaisowurtzitane residue.

Meanwhile, the nitroso group-containing hexaazaisowurtzitane derivative represented by general formula (III) may be prepared by nitrosation of $W A_n H_{(6-n)}$ as shown in the following reaction formula (2):

$$W A_n H_{(6-n)} \rightarrow W A_n NS_{(6-n)} \qquad (2)$$

wherein n is an integer of 4 or 5, A is an acyl group having 1–10 carbon atoms with each acyl group being the same as or different from one or more of the others, H is a hydrogen atom, NS is a nitroso group and W is a hexavalent hexaazaisowurtzitane residue.

Any acyl group-containing hexaazaisowurtzitane derivative represented by $W A_n H_{(6-n)}$ or $W A_m H_{(6-m)}$ in the above reaction formula (1) or (2) may be used as a starting material, regardless of its method of preparation. It is, however, preferable to use $W A_n H_{(6-n)}$ or $W A_m H_{(6-m)}$ which is prepared by reductive dearylmethylation of $W B_6$ in the presence of an acylating agent and further reductive dearylmethylation of the resultant product in the absence of an acylating agent, for example, as described in PCT publication No. WO96/23792. The process for preparing the above-mentioned starting materials will be given in more detail later.

The acyl groups of the hexaazaisowurtzitane derivatives $W A_n H_{(6-n)}$ and $W A_m H_{(6-m)}$ which are the starting materials in the reaction formulae (1) and (2) are those having 1–10 carbon atoms, in which each acyl group may be the same as or different from one or more of the others. Examples of the acyl groups include acetyl, formyl, propionyl, butyryl, isobutyryl, valeryl, hexanoyl, 2-phenylacetyl and the like. Preferred acyl groups are those having 1–5 carbon atoms such as formyl, acetyl, propionyl, butyryl, valeryl and the like and more preferred acyl groups are those having 2–4 carbon atoms such as acetyl, propionyl, butyryl and the like.

Each of these hexaazaisowurtzitane derivatives may comprise any of various isomers according to difference in the positions of acyl groups and hydrogen atoms thereof; however, any of such isomers may be used according to the present invention.

The derivatives represented by the formula $W A_m H_{(6-m)}$ includes $W A_4 H_2$, $W A_5 H_1$ and $W A_6$, which may be used independently or as a mixture of two or more.

As the nitrating agent for the nitration process of reaction formula (1), any nitrating agent may be used as far as it can nitrate $W A_m H_{(6-m)}$. Examples of such nitrating agents include nitric acid, dinitrogen tetroxide, nitric acid-nitration accelerator mixtures, dinitrogen pentoxide and the like. These nitrating agents may be used as a mixture of two or more. Among the above-mentioned nitrating agents, nitric acid may be partially or fully substituted with a metal nitrate such as silver nitrate or the like or a nitronium salt such as nitronium tetrafluoroborate or the like. Use of nitric acid, dinitrogen tetroxide or dinitrogen pentoxide is preferred because of enhancing selectivity in the nitration of reaction formula (1).

The nitration accelerators are those that increase the electrophilicity of nitronium ions. Examples of the accelerators which may be used according to the present invention normally include:

A. Organic acids having 'perfluoro' structures such as trifluoroacetic acid and the like, strong organic or inorganic Bronsted acids, of which typical examples are sulfuric acid, fuming sulfuric acid, perfluoroalkylsulfonylimides polyphosphoric acid, trifluoromethanesulfonic acid and the like;

B. Carboxylic anhydrides such as trifluoroacetic anhydride, acetic anhydride and the like;

C. Oxides such as diphosphorus pentoxide, dinitrogen pentoxide and sulfur trioxide and the like; and D. Lewis acids such as rare earth salts of perfluoroalkylsulfonylimides, rare earth salts of perfluoroalkylsulfonic acids and the like.

The above-mentioned nitration accelerators may be used as a mixture of two or more. Among the nitration accelerators described under items A through C above, the strong Brønsted acids of item A and oxides of item C are preferred because they increase nitration reaction rate. The strong Brønsted acids of item A are more preferable if they have the same acidity as or are stronger than that of trifluoroacetic acid (e.g., in terms of pKa). Among the nitration accelerators of items A through C, sulfuric acid, trifluoroacetic acid, polyphosphoric acid, diphosphorus pentoxide and sulfur trioxide are especially preferred.

The above-mentioned perfluoroalkylsulfonylimides are represented by the following formula (IX):

$$Rf SO_2 NH SO_2 Rf' \qquad (IX)$$

wherein Rf and Rf' are perfluoroalkyl groups having 1–8 carbon atoms, S is a sulfur atom, O is an oxygen atom, N is a nitrogen atom and H is a hydrogen atom.

The perfluoroalkyl groups of the perfluoroalkylsulfonylimides may be straight or branched and one or more of such imides may be used at the same time. Examples of the imides include bis-(trifluoromethylsulfonyl)imide, bis-(nonafluoro-butylsulfonyl)imide, bis-(heptadecafluorooctylsulfonyl)imide and the like.

Further, the rare earth salts of perfluoroalkylsulfonic acids may be used as the nitration accelerators of the present invention and are represented by formula (X):

$$M(Rf SO_3)_3 \qquad (X)$$

wherein Rf is a perfluoroalkyl group having 1–8 carbon atoms, S is a sulfur atom, O is an oxygen atom and M is a rare earth element.

Examples of the rare earth salts of perfluoroalkylsulfonic acids include tris-(trifluoromethylsulfone)lanthanum (III), tris-(trifluoromethylsulfone)ytterbium (III), tris-(trifluoromethyl-sulfone)europium (III), tris-(trifluoromethylsulfone)yttrium (III), tris-(trifluoromethylsulfone)scandium (III), tris-(trifluoromethylsulfone) praseodymium and the like.

Still further, there may be used the rare earth salts of perfluoroalkylsulfonylimides represented by the following formula (XI):

$$M(Rf SO_2 N SO_2 Rf')_3 \qquad (XI)$$

wherein Rf and Rf' are perfluoroalkyl groups having 1–8 carbon atoms, S is a sulfur atom, O is an oxygen atom, N is a nitrogen atom and M is a rare earth element.

The perfluoroalkyl groups of the perfluoroalkylsulfonylimides may be straight or branched and one or more of such imides may be used at the same time.

The rare earth salts of perfluoroalkylsulfonylimides are Lewis acids, which are stable in water and which may be recovered for reuse after reaction.

Examples of the rare earth salts of perfluoroalkylsulfonylimides which are rare earth element-containing Lewis acids include tris-(bis-(trifluoromethylsulfonyl)imide lanthanum (III), tris-(bis-(trifluoromethylsulfonyl)imide ytterbium (III), tris-(bis-(trifluoromethylsulfonyl)imide yttrium (III), tris-(bis-(nonafluorobutylsulfonyl)imide)ytterbium (III), tris-(bis-(nonafluorobutylsulfonyl)imide) yttrium (III), tris-(bis-(nonafluorobutylsulfonyl)imide) yttrium (III), tris-(bis-(nonafluorobutylsulfonyl)imide) lanthanum (III), tris-(bis-(heptadeca-fluorooctylsulfonyl)imide) lanthanum (III ), tris-(bis-(heptadeca-fluorooctylsulfonyl)imide) ytterbium (III), tris-(bis-(heptadeca-fluorooctylsulfonyl)imide) yttrium (III) and the like.

The rare earth salts of perfluoroalkylsulfonylimides are salts of perfluoroalkylsulfonylimides and rare earth elements. Any element may be acceptable so long as it is a rare earth element, but preferred examples of the rare earth elements include lanthanum, ytterbium, yttrium and the like.

The above-mentioned nitration accelerators are homogeneous or heterogeneous, either of which may be used. For example, the following nitration accelerators are preferably used since they may be easily recovered:

E. Polymeric solid Brønsted acids such as Nafion-NR50 (trade name, Du Pont) and the like, strong Brønsted acids such as zeolites and the like;

F. Organic solid Lewis acids such as rare earth salts of perfluoroalkylsulfonylimides having long-chain fluoroalkyl groups;

G. Liquid perfluoroalkanesulfonic acids and oligosulfonic acids having 'perfluoro' skeletons which are not homogeneously soluble in reaction systems.

Typical examples of the above-mentioned zeolites which may be used according to the present invention include analcime, bikataite, brewsterite, chabazite, clinoptilobite, bachiardite, edingtonite, epistilbite, erionite, faujasite, ferrierite, gismondine, gmelinite, gonnardite, harmontome, heulandite, kieselguhr, laumontite, levynite, losod, mesolite, mordenite, natrolite, omega, paulingite, philipsite, scolecite, sodalitehydrate, stilbite, thomsonite and yugawaralite. Examples of synthetic zeolite compounds which may also be used according to the present invention include "A", "N-A", "L$^b$","P", "T", "X", "ZX-4", "ZX-5", "ZSM-5", "ZSM-11", "MCM-22", "faujasite" "Linde type L" and the like.

As the strong Brønsted acids, insoluble sulfonic group-containing polymers and sulfonic group-containing cation-exchange resins may be used as well.

Insoluble sulfonic group-containing polymers and sulfonic group-containing cation-exchange resins are also strongly acidic solid catalysts that may be recovered for reuse after reaction. Examples of the insoluble sulfonic group-containing polymers and sulfonic group-containing cation-exchange resins include polyethylenesulfonic acid, sulfonic group-containing fluoro-polymers and the like. As preferred example there are insoluble sulfonic group-containing polymers such as sulfonic group-containing fluoropolymers of which the repeating unit is represented by the following general formula (XII):

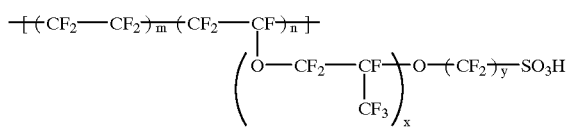

(XII)

cation-exchange resins and the like. Preferred examples of insoluble sulfonic group-containing polymers and cation-exchange resins include Nafion-NR50 (trade name, Du Pont) and the like.

The nitration of reaction formula (1) may be carried out in the presence of a solvent, though it may be performed in the absence of the solvent. Any solvent may be used unless it adversely affects the nitration of the starting material. Examples of the solvents which may be employed include halides such as dichloromethane, chloroform and the like; polar solvents such as acetonitrile, sulfolane, dimethylformamide, dimethyl-acetamide and the like; ethers such as tetrahydrofuran, diethyl ether and the like; esters such as ethyl acetate, methyl acetate, ethyl propionate and the like; ketones such as acetone, methyl ethyl ketone, ethyl isobutyl ketone and the like. These solvents may be used independently or as a mixture of two or more.

The process of reaction formula (1) is carried out at a temperature between −20 and 80 degrees C. and preferably between 0 and 60 degrees C. Reaction time ranges from 0.5 to 10 hours and preferably from 1 to 8 hours.

The quantity of the nitrating agent which is used in the process of reaction formula (1) normally ranges from 2.0 to 500 and preferably 3.0 to 400 in terms of the molar ratio of said agent to $W A_m H_{(6-m)}$. The quantity of the nitration accelerator used in the process ranges from 1.0 to 500 and preferably from 1.5 to 300 in terms of the molar ratio of said accelerator to $W A_m H_{(6-m)}$.

Any acyl group-containing hexaazaisowurtzitane derivative represented by $W A_n H_{(6-n)}$ in the nitrosation of reaction formula (2) may be used as a starting material, irrespective of its method of preparation. It is however preferable to use the derivative $W A_n H_{(6-n)}$ which is prepared by reductive dearylmethylation of $W B_6$ in the presence of an acylating agent and further reductive dearylmethylation of the resultant product in the absence of an acylating agent, for example, as described in PCT publication No. WO96/23792. This process will be described later in more detail.

As the starting material for the nitrosation of reaction formula (2), there are $W A_4 H_2$ and $W A_5 H_1$, which may be used independently or as a mixture of the two. $W A_4 H_2$ and $W A_5 H_1$ may be mixed with each other at any ratio and easily converted into nitroso compounds because they can be respectively nitrosated in the same manner.

As the agent for the process shown in reaction formula (2), any nitrosating agent may be used so long as it can nitrosate $W A_n H_{(6-n)}$ to produce $W A_n NS_{(6-n)}$. For example, there may be used nitrosating agents such as nitrous acid, dinitrogen tetroxide, nitrosonium salts, nitrosyl chloride and the like, of which nitrosonium ions are strong in electrophilicity. Nitrous acid may be used as it is, or a mixture may be used which consists of a nitrite such as sodium nitrite, potassium nitrite or the like and an acid such as acetic acid, hydrochloric acid or the like. Nitrosonium salts such as nitrosonium tetrafluoroborate, nitrosonium hexafluorophosphate and the like may be preferably used since the salts of such fluoride ions are negative, and raise the electrophilicity of nitrosonium ions. The quantity of the nitrosating agent which may be added according to the present invention ranges from 1 to 200 moles, preferably from 3 to 150 moles and more preferably from 4 to 100 moles per mole of $W A_n H_{(6-n)}$.

The nitrosation of reaction formula (2) is carried out normally in the presence of a solvent, though it may be performed in the absence of the solvent. Any solvent may be used unless it has an adverse influence on the nitrosation. Examples of the solvents which may be used include halides such as dichloromethane, chloroform, carbon tetrachloride and the like; polar solvents such as acetonitrile, sulfolane, dimethyl-formamide, dimethylacetamide and the like; carboxylic acids such as acetic acid, propionic acid and the like;

carboxylic anhydrides such as acetic anhydride, propionic anhydride and the like; ethers such as tetrahydrofuran, diethyl ether and the like; esters such as ethyl acetate, methyl acetate, ethyl propionate and the like; ketones such as acetone, methyl ethyl ketone, ethyl isobutyl ketone and the like; water, pyridine and the like. These solvents may be used independently or as a mixture of two or more.

The nitrosation of reaction formula (2) may be performed at temperatures ranging from −50 to 200 degrees C., preferably from −30 to 150 degrees C. and more preferably from −20 to 100 degrees C.

Incidentally, the nitro group-containing hexaazaisowurtzitane derivatives of formula (I) may also be prepared by nitration of $W A_n NS_{(6-n)}$ obtained according to reaction formula (2) by use of a nitrating agent, as indicated in the following reaction formula (3):

$$W A_n NS_{(6-n)} \rightarrow W A_n N_{(6-n)} \quad (3)$$

wherein n is an integer of 4 or 5, A is an acyl group having 1–10 carbon atoms with each acyl group being the same as or different from one or more of the others, NS is a nitroso group, N is a nitro group and W is a hexavalent hexaazaisowurtzitane residue.

As the starting material in the nitration of reaction formula (3), there are $W A_4 NS_2$ and $W A_5 NS_1$, which may be used independently or as a mixture of the two. Since the $W A_4 NS_2$ and $W A_5 NS_1$ can be respectively nitrated in the same manner, the mixture may consist of them at any ratio. Mixtures containing $W A_4 NS_1 H_1$ which may be produced during the reaction of reaction formula (2) and $W A_4 H_2$ and $W A_5 H_1$ which remain unreacted during said reaction may be used as the starting materials for the reaction of reaction formula (3).

For the process of reaction formula (3), the same nitrating agent, solvent and reaction conditions including reaction temperature and the like as those described above for the nitration of reaction formula (1) may be employed.

The $W A_n H_{(6-n)}$ which is the starting material in reaction formulae (1) and (2) above may be obtained according to the process of the following reaction formula (4):

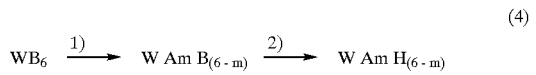

(4)

Step 1: reductive dearylmethylation in the presence of an acylating agent

Step 2: reductive dearylmethylation in the absence of an acylating agent wherein m is an integer of 4–6, A is an acyl group having 1–10 carbon atoms with each acyl group being the same as or different from one or more of the others, B is an arylmethyl group, H is a hydrogen atom and W is a hexavalent hexaazaisowurtzitane residue.

That is to say, $W A_m H_{(6-m)}$ may be prepared by reductive dearylmethylation of $W B_6$ in the presence of an acylating agent to obtain $W A_m B_{(6-m)}$ (step 1) and further by reductive dearylmethylation of the resultant $W A_m B_{(6-m)}$ (step 2).

In step 1 of reaction formula (4), the reductive dearylmethylation of $W B_6$ with an acylating agent is normally carried out in the presence of a reducing agent by contact with a reduction catalyst. In this case, any combination of a reducing agent and a catalyst may be used so long as the combination can proceed with the dearylmethylation of $W B_6$. As the reducing agents, hydrogen, formic acid and the like may be used and preferably hydrogen is used. Examples of the catalysts which may be used include platinum metals and derivatives thereof, preferably there may be used Pd and its derivatives such as $Pd(OAc)_2$, $PdCl_2$, $Pd(NO_3)_2$, PdO, $Pd(OH)_2$, $Pd_3Pb_1$, $Pd_3Te_1$, and the like and Ru and its derivatives such as $RuCl_3$ and the like and more preferably there may be used Pd and its derivatives such as $Pd(OAc)_2$, $PdCl_2$ and the like. These catalysts may be used as they are or supported by carriers such as active carbon, silica, alumina, silica-alumina, zeolite, activated clay and the like. These catalysts may be subjected to reduction treatment before use in the reaction. If the catalysts are solid, their surface acidic sites may be inactivated by silylation or acylation treatment, while their surface acidity may be changed by adsorption of alkaline materials such as NaOH and the like. The quantity of the catalyst may depend upon the reduction activity thereof but the catalyst may be used normally in the range of 0.0001 to 20 and preferably 0.001 to 10 in terms of the weight ratio of the metal content of the catalyst to $W B_6$.

Any acylating agent may be used in step 1 of reaction formula (4) so long as it can acylate secondary amines. Examples of the acylating agents include carboxylic acid esters of N-hydroxysuccinimide such as N-acetoxysuccinimide, N-propionyloxysuccinimide, N-(2-phenyl-acetoxy)succinimide and the like; carboxylic anhydrides such as acetic anhydride, propionic anhydride, butyric anhydride, acetic anhydride-formic anhydride mixtures and the like; acylimidazoles such as acetylimidazole, propionylimidazole and the like; mixtures of phenyl bromide carboxylic anhydrides such as mixtures of phenyl bromide and acetic anhydride and the like. Among these acylating agents, carboxylic acid esters of N-hydroxysuccinimide (N-hydroxy-succinimide esters) such as N-acetoxysuccinimide, N-propionyloxysuccinimide and the like are preferably used because said esters increase the selective production of $W A_6$. These acylating agents may be used independently or as a mixture of two or more. Mixtures of the N-hydroxysuccinimide carboxylic acid esters such as N-acetoxysuccinimide, N-propionylsuccinimide and the like and the carboxylic anhydrides such as acetic anhydride, propionic anhydride and the like are especially preferable since said mixtures not only raise the reaction rate of step 1 in reaction formula (4) but also enhance the selective production of $W A_4 H_2$ and $W A_5 H_1$.

In the step 1 of reaction formula (4), the quantity of the acylating agent depends upon its reaction method and reaction conditions but ranges from 4 to 100 and preferably from 4.5 to 50 in terms of the molar ratio of the agent to the arylmethyl groups of $W B_6$. When a mixture of an N-hydroxysuccinimide ester and a carboxylic anhydride is used as the acylating agent, the quantity of the carboxylic anhydride ranges from 0.01 to 100 and preferably from 0.1 to 10 in terms of the molar ratio of the anhydride to the ester.

As solvents used in step 1 of reaction formula (4), any solvent may be used if it dissolves $W B_6$ and if it does not adversely affect the reaction. Examples of the solvents include aromatic compounds such as benzene, toluene, ethylbenzene, xylene, cumene, cymene, diisopropyl benzene, phenyl ethyl ether and the like; amide compounds such as dimethylacetamide and the like; cyclic, straight and branched ethers such as tetrahydrofuran, dioxane, tetrahydropyran, diethyl ether, dipropyl ether, diisopropyl ether, ethyleneglycol diethylether, diethyleneglycol dimethylether and the like; and aliphatic alcohols such as methanol, ethanol, propanol, isopropyl alcohol, t-butyl alcohol and the like. These solvents may be used independently or as a mixture of two or more. Among them, aromatic compounds such as benzene, toluene, ethylbenene, xylene and the like may be preferably used since they increase the reaction rate of the dearylmethylation of $W B_6$.

In step 1 of reaction formula (4), the quantity of the solvent may depend upon its solvent power and the reaction temperature therein, but the solvent may be used in the range of 0.1 to 100 and preferably 1 to 100 in terms of the weight ratio of said solvent to $W B_6$.

In step 1 of reaction formula (4), the reaction pressure ranges normally from 0.01 to 100 Mpa and preferably from 0.1 to 30 MPa. If hydrogen is used as the reducing agent, the higher the reaction pressure is, the more the reaction rate is increased in some cases and the reaction pressure should therefore be set in the range of preferably 0.01 to 50 MPa and more preferably 0.1 to 20 MPa in terms of a partial pressure of the hydrogen. Inert gases such as nitrogen, argon, helium and the like may be present in addition to hydrogen.

The reaction temperature of step 1 of reaction formula (4) normally ranges from −20 to 300 degrees C. and preferably 0 to 200 degrees C.

The reaction time of step 1 of reaction formula (4) may vary with the catalyst, acylating agent, solvent and reaction conditions which are employed in said step but normally ranges from 0.1 to 500 hours and preferably from 1 to 200 hours.

In step 2 of reaction formula (4), any benzyl group-containing hexaazaisowurtzitane derivative may be employed as $W A_m B_{(6-m)}$ used for the reductive dearylmethylation irrespective of its method of preparation.

Any process may be applied to step 2 in reaction formula (4) so long as it is capable of advancing the dearylmethylation of the $W A_m B_{(6-m)}$. The dearylmethylation is normally performed in the presence of a reducing agent by contact of said agent with a reduction catalyst.

As the reducing agent, hydrogen, hydrazine, formic acid and the like may be used and preferably hydrogen is used. As the catalysts, platinum metals and their derivatives may be used. Preferably there may be used Pd and its derivatives such as $Pd(OAc)_2$, $PdCl_2$, $Pd(NO_3)_2PdO$, $Pd(OH)_2$, $Pd_3Pb_1$, $Pd_3Te_1$ and the like and Ru and its derivatives such as $RuCl_3$ and the like, and more preferably there may be used Pd and its derivatives such as $Pd(OAc)_2$, $PdCl_2$ and the like. These catalysts may be used as they are or supported by carriers such as activated carbon, silica, alumina, silica-alumina, zeolite, activated clay and the like. The catalysts may be subjected to reduction treatment before use for the reaction. If the catalysts are solid, the surface acidic sites thereof may be inactivated by silylation or acylation treatment, while the surface acidity thereof may be changed by adsorption of alkaline materials such as NaOH and the like.

In step 2 of reaction formula (4), the quantity of the catalyst may depend upon the reducing activity thereof but the catalyst may be used in the range of 0.0001 to 10 and preferably 0.001 to 1 in terms of weight ratio of the metal content of said catalyst to $W A_m B_{(6-m)}$.

As the solvent used in step 2 of reaction formula (4), any solvent may be used if it dissolves $W A_m B_{(6-m)}$ and if it does not adversely affect the reductive dearylmethylation. Examples of the solvents include carboxylic acids such as acetic acid, propionic acid, butyric acid and the like; amide compounds such as dimethylacetamide and the like; and amines such as N,N-dimethylaniline and the like. These solvents may be used independently or as a mixture of two of more. Carboxylic acids such as acetic acid, propionic acid and the like may be preferably used from the viewpoint of reaction rate.

In step 2 of reaction formula (4), the quantity of the solvent to be used may vary with its solvent power and the reaction temperature, but the solvent may be used in the range of 1 to 500 and preferably 5 to 100 as a weight ratio of said solvent to the $W A_m B_{(6-m)}$.

The reaction pressure of step 2 of reaction formula (4) ranges normally from 0.01 to 100 MPa and preferably from 0.1 to 10 MPa. If hydrogen is used as the reducing agent, the reaction pressure of the step should be set in the range of preferably 0.01 to 50 MPa and more preferably 0.1 to 10 MPa in terms of hydrogen partial pressure. Inert gases such as nitrogen, argon, helium and the like may be present in addition to hydrogen.

The reaction temperature of step 2 of reaction formula (4) normally ranges from −20 to 300 degrees C. and preferably 0 to 200 degrees C.

The reaction time of step 2 of reaction formula (4) may vary with the catalyst, acylating agent, solvent, and other conditions which are employed in the step but normally ranges from 0.1 to 500 hours and preferably from 1 to 200 hours.

Hereinbelow, there will be described a process for preparing hexanitrohexaazaisowurtzitane from hexaazaisowurtzitane derivatives of general formula (I) or (III). Hexanitrohexaazaisowurtzitane is easily prepared by nitration of hexaazaiowurtzitane derivatives of general formula (I) or (III).

Firstly, as shown in the following reaction formula (5), hexanitrohexaazaisowurtzitane can be prepared by nitration of a derivative of general formula (I):

$$W A_n N_{(6-n)} \rightarrow W N_6 \qquad (5)$$

As the starting material used in the process of reaction formula (5), there are $W A_4 N_2$ and $W A_5 N_1$, which may be used independently or as a mixture of the two. The starting material may contain $W A_4 N_1 H_1$, $W A_3 N_3$, $W A_2 N_4$ and $W A_1 N_5$ which are possibly produced in the process of reaction formula (1) and $W A_4 H_2$, $W A_5 H_1$ and $W A_6$ which remain unreacted after said process. For the process of reaction formula (5), the same nitration accelerators, solvent and reaction conditions including reaction temperature and the like as those described above for the nitration of reaction formula (1) may be employed. The same nitrating agent as that described for the nitration of reaction formula (1) may be used in the process, and a mixture of nitric acid and a nitration accelerator is preferably used as a nitrating agent since the reaction rate of the nitration can be increased. When a nitrating agent consisting of nitric acid and a nitration accelerator is used, the quantity of the nitric acid normally ranges from 6.0 to 500 and preferably from 9 to 400 in terms of the molar ratio of the nitric acid to $W A_m H_{(6-m)}$. The reaction temperature is in the range of −20 to 140 degrees C. and preferably 0 to 120 degrees C. The reaction time of reaction formula (5) ranges from 0.5 to 120 hours and preferably from 1 to 50 hours.

Secondly, as shown in the following reaction formula (6), hexanitrohexaazaisowurtzitane can be prepared by nitration of a nitroso group-containing hexaazaisowurtzitaine derivative represented by general formula (III).

$$W A_n NS_{(6-n)} \rightarrow W N_6 \qquad (6)$$

As the starting material in the nitration of reaction formula (6), there may be $W A_4 NS_2$ and $W A_5 NS_1$, which may be used independently or as a mixture of the two. The starting material may contain $W A_4 NS_1 H$ which is possibly produced in the process of reaction formula (2) and $W A_4 H_1$ and W $A_5$ $H_1$ which remain unreacted. The process of reaction formula (6) may be carried out with the same nitrating agent, solvent, and reaction temperature and other reaction conditions as those described for the nitration of reaction formula (1).

Instead of a stepwise reaction process consisting of combinations such as reaction formulae (1) and (5), (2) and (6), or (2), (3) and (5), hexanitrohexaazaisowurtzitane may also be prepared by a single-step process for nitration of W $A_m$ $H_{(6-m)}$ under the same conditions as those described above for reaction formula (5) or (6) as shown in the following reaction formula (7):

$$W A_m H_{(6-m)} \rightarrow W N_6 \qquad (7)$$

wherein m is an integer of 4–6, A is an acyl group having 1–10 carbon atoms with each acyl group being the same as or different from one or more of the others, H is a hydrogen atom, N is a nitro group and W is a hexavalent hexaazaisowurtzitane residue.

For the process of reaction formula (7), the same starting material, nitrating agent, solvent, reaction conditions and the like as those described above for the nitration in reaction formula (1) may be employed. The reaction temperature of the process ranges normally from −20 to 140 degrees C. and preferably from 0 to 120 degrees C. The reaction time of the process ranges from 0.5 to 120 hours and preferably from 1 to 50 hours.

The hexaazaisowurtzitane derivatives of formulae (I) and (III) which can be prepared according to the present invention are useful as precursors of hexanitrohexaazaisowurtzitane which is a high-performance explosive.

EXAMPLES

Hereinbelow, the present invention will be described in more detail with reference to the following examples but they should not be construed to limit the scope of the present invention.

Example 1

$$W A_4 H_2 \rightarrow W N_6$$

A 200 ml reactor was placed in a 0° C. water bath. To the reactor, 17.50 grams of 97% sulfuric acid were added and then, 5.63 grams of 98% nitric acid were slowly dropped into the reactor while agitating with a stirrer. To the resulting mixture, 1.00 gram of tetraacetylhexaazaisowurtzitane was added. The resultant mixture was heated to 60 degrees C. and was then reacted for 24 hours. After reaction, the resulting reaction solution was dropped into 250 grams of ice water. The resulting mixture was left at rest and was filtered through a membrane filter to obtain a solid reaction product. The product was washed with 250 grams of purified water to obtain 1.28 grams of hexanitrohexaazaisowurtzitane in a 98 percent yield. The structure of the product was analyzed as follows.

As a result of infrared (IR) absorption spectroscopy of a specimen prepared from the product according to a KBr tablet method, there were confirmed an IR absorption in the vicinity of 1,605 $cm^{-1}$ ascribed to the antisymmetrical stretching vibration of nitro groups, two IR absorptions in the vicinity of 1,325 $cm^{-1}$ and 1,270 $cm^{-1}$ ascribed to the symmetrical stretching vibration of nitro groups, two IR absorptions in the vicinity of 945 $cm^{-1}$ and 880 $cm^{-1}$ ascribed to the bending vibration of nitro groups and an IR absorption in the vicinity of 3,030 $cm^{-1}$ ascribed to the stretching vibration of methine groups of the hexaazaisowurtzitane skeleton (hereinafter referred to as W skeleton).

These IR absorption-spectrum characteristics were identical with those of the hexanitrohexaazaisowurtzitane described in "COMBUSTION AND FLAME 87", 145–151, 1991.

Incidentally, an IR absorption in the vicinity of 1,680 $cm^{-1}$ vanished, which was ascribed to the carbonyl groups (C═O) of the acetyl groups contained in the tetraacetylhexaazaisowurtzitane which was used as the starting material.

It was learned from the above analysis that hexanitrohexaazaisowurtzitane as produced by substituting the acetyl groups of tetraacetylhexaazaisowurtzitane with nitro groups.

Incidentally, as a result of analyzing the product by high performance liquid chromatography in the same manner as described in "INTERNATIONAL SYMPOSIUM ON ENERGETIC MATERIAL TECHNOLOGY PROCEEDINGS", September. 24–27, 76–81, 1995, which is a publication on the properties and characteristics of hexanitrohexaazaisowurtzitane, it was found that the retention time of the product was the same as that described in the publication.

Furthermore, by the EI-mass spectroscopy of the product, there were confirmed 392 (parent ion-$NO_2$) as a fragment ion peak, and 316, 213 and 46 ($NO_2$) as ion peaks. These ion peaks were also identical with those described in the above-mentioned publication "INTERNATIONAL SYMPOSIUM ON ENERGETIC MATERIAL TECHNOLOGY PROCEEDINGS", September. 24–27, 76–81, 1995.

Example 2

$$W A_5 H_1 \rightarrow W N_6$$

A 200 ml reactor was placed in a 0° C. water bath. To the reactor, 15.56 grams of 97% sulfuric acid were added and then, 5.00 grams of 98% nitric acid were slowly dropped into the reactor while agitating with a stirrer. To the resulting mixture, 1.00 gram of pentaacetylhexaazaisowurtzitane was added to prepare a mixture. The mixture was heated to 60 degrees C. and was then reacted for 24 hours. After reaction, the resultant reaction solution was added to 250 grams of ice water. The resulting mixture was left at rest and was filtered through a membrane filter to obtain a solid. The solid was washed with 250 grams of purified water to obtain 1.14 gram of hexanitrohexaazaisowurtzitane in a 98 percent yield.

As a result of structural analysis of the solid in the same manner as described in Example 1, it was found that hexanitrohexaazaisowurtzitane was produced.

Example 3

$$W A_6 \rightarrow W N_6$$

A 200 ml reactor was placed in a 0° C. water bath. To the reactor, 14.00 grams of 97% sulfuric acid were added and then, 4.50 grams of 98% nitric acid were slowly dropped into the reactor while agitating with a stirrer. To the resulting mixture, 1.00 gram of hexaacetylhexaazaisowurtzitane was added to prepare a mixture. The mixture was heated to 60 degrees C. and was then reacted for 24 hours. After reaction, the resultant reaction solution was dropped into 250 grams of ice water. The resulting mixture was left at rest and was filtered through a membrane filter to obtain a solid. The solid was washed with 250 grams of purified water to obtain 1.02 grams of hexanitrohexaazaisowurtzitane in a 98 percent yield.

As a result of structural analysis of the solid in the same manner as described in Example 1, it was found that hexanitrohexaazaisowurtzitane was produced.

Example 4

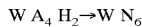

A 200 ml reactor was placed in a 0° C. water bath. To the reactor, 22.50 grams of 98% nitric acid were added and then, 6.11 grams of trifluoroacetic acid were added thereto while agitating with a stirrer. To the resulting solution, 1.00 gram of tetraacetylhexaazaisowurtzitane was added to obtain a mixture. The mixture was heated to 100 degrees C. and was then reacted for 3 hours. After reaction, the resulting reaction solution was subjected to solvent evaporation to obtain a solid. The solid was neutralized with a 10% aqueous solution of $NaHCO_3$, washed with water and dried to recover the solid. The solid was dissolved in acetonitrile and was analyzed by high performance liquid chromatography. As a result, it was confirmed that hexanitrohexaazaisowurtzitane was produced in a 20 percent yield.

Further, the structure of the solid was analyzed in the same manner as described in Example 1 and it was found that hexanitrohexaazaisowurtzitane was produced.

Example 5

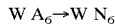

A 200 ml reactor was placed in a 0° C. water bath. To the reactor, 18.00 grams of 98% nitric acid were added and then, 8.14 grams of trifluoroacetic acid were added thereto while agitating with a stirrer. To the resulting solution, 1.00 gram of hexaacetylhexaazaisowurtzitane was added to obtain a mixture. The mixture was heated to 100 degrees C. and was then reacted for 3 hours. After reaction, the resulting solution was subjected to solvent evaporation to obtain a solid. The solid was neutralized with a 10% aqueous solution of $NaHCO_3$, washed with water and dried to recover the solid. The solid was dissolved in acetonitrile and was analyzed by high performance liquid chromatography. As a result, it was confirmed that hexanitrohexaazaisowurtzitane was produced in an 18 percent yield.

Further, the structure of the solid was analyzed in the same manner as described in Example 1 and it was found that hexanitrohexaazaisowurtzitane was produced.

Example 6

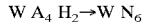

A 200 ml reactor was placed in a 0° C. water bath. To the reactor, 11.25 grams of 98% nitric acid were added and then, 7.14 grams of sulfuric anhydride were added thereto while agitating with a stirrer. To the resulting solution, 1.00 gram of tetraacetylhexaazaisowurtzitane was added to prepare a mixture. The mixture was heated to 60 degrees C. and was then reacted for 24 hours. After reaction, the resultant reaction solution was added to 250 grams of ice water. The resulting mixture was left at rest and was filtered through a membrane filter to obtain a solid. The solid was washed with 250 grams of purified water to obtain 1.29 grams of hexanitrohexaazaisowurtzitane in a 99 percent yield.

As a result of structural analysis of the solid in the same manner as described in Example 1, it was found that hexanitrohexaazaisowurtzitane was produced.

Example 7

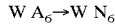

A 200 ml reactor was placed in a 0° C. water bath. To the reactor, 18.00 grams of 98% nitric acid were added and then, 5.71 grams of sulfuric anhydride were added thereto while agitating with a stirrer. To the resulting solution, 1.00 gram of hexaacetylhexaazaisowurtzitane was added to prepare a mixture. The mixture was heated to 60 degrees C. and was then reacted for 24 hours. After reaction, the resultant reaction solution was added to 250 grams of ice water. The resulting mixture was left at rest and was filtered through a membrane filter to obtain a solid. The solid was washed with 250 grams of purified water to obtain 1.03 gram of hexanitrohexaazaisowurtzitane in a 99 percent yield.

The structure of the solid was analyzed in the same manner as described in Example 1 and it was found that hexanitrohexaazaisowurtzitane was produced.

Example 8

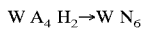

A 200 ml reactor was placed in a 0° C. water bath. To the reactor, 22.50 grams of 98% nitric acid were added and then, 12.67 grams of diphosphorus pentoxide were added thereto while agitating with a stirrer. To the resulting solution, 1.00 gram of tetraacetylhexaazaisowurtzitane was added to prepare a mixture. The mixture was heated to 100 degrees C. and was then reacted for 3 hours. After reaction, the resultant reaction solution was dropped into 250 grams of ice water. The resulting mixture was left at rest to form a precipitate. The precipitate was filtered out from the resulting solution and was washed with water to recover the precipitate. The precipitate was dissolved in acetonitrile and was analyzed by high performance liquid chromatography. As a result, it was confirmed that hexanitrohexaazaisowurtzitane was produced in a 11 percent yield.

The structure of the precipitate was analyzed in the same manner as described in Example 1 and it was found that hexanitrohexaazaisowurtzitane was produced.

Example 9

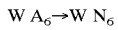

A 200 ml reactor was placed in a 0° C. water bath. To the reactor, 18.00 grams of 98% nitric acid were added and then, 10.14 grams of diphosphorus pentoxide were added thereto while agitating with a stirrer. To the resulting solution, 1.00 gram of hexaacetylhexaazaisowurtzitane was added to prepare a mixture. The mixture was heated to 100 degrees C. and was then reacted for 3 hours. After reaction, the resultant reaction solution was dropped into 250 grams of ice water. The resulting mixture was left at rest to form a precipitate. The precipitate was extracted by filtration from the resulting mixture and was washed with water to recover the precipitate. The precipitate was dissolved in acetonitrile and was analyzed by high performance liquid chromatography. As a result, it was confirmed that hexanitrohexaazaisowurtzitane was produced in a 9 percent yield.

The structure of the precipitate was analyzed in the same manner as described in Example 1 and it was found that hexanitrohexaazaisowurtzitane was produced.

Example 10

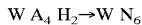

A 200 ml reactor was placed in a 0° C. water bath. To the reactor, 22.50 grams of 98% nitric acid were added and then, 11.25 grams of Nafion-NR50 were added thereto while agitating with a stirrer. To the resulting solution, 1.00 gram of tetraacetylhexaazaisowurtzitane was added to prepare a mixture. The mixture was heated to 100 degrees C. and was then reacted for 3 hours. After reaction, the resultant reaction solution was dropped into 250 ml of water. The resultant mixture was left at rest to form a precipitate. The precipitate was extracted by filtration from the resulting mixture, washed with 250 ml of purified water, extracted by filtration and added to 50 ml of acetone. The resulting mixture was stirred and was filtered to recover the Nafion-NR50. The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 70 percent yield.

The structure of the product was analyzed in the same manner as described in Example 1 and it was found that hexanitrohexaazaisowurtzitane was produced.

Example 11

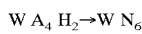

A 200 ml reactor was placed in a 0° C. water bath. To the reactor, 20.00 grams of 98% nitric acid were added and then, 10 grams of Nafion-NR50 were added thereto while agitating with a stirrer. To the resulting solution, 1.00 gram of tetraacetylhexaazaisowurtzitane was added to prepare a mixture. The mixture was heated to 100 degrees C. and was then reacted for 3 hours. After reaction, the resultant reaction solution was dropped into 250 ml of water. The resulting mixture was left at rest to form a precipitate. The precipitate was filtered out from the mixture, washed with 250 ml of purified water, filtered out and added to 50 ml of acetone. The resulting mixture was stirred and was filtered to recover the above-mentioned Nafion-NR50. The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 55 percent yield.

The structure of the product was analyzed in the same manner as described in Example 1 and it was found that hexanitrohexaazaisowurtzitane was produced.

Example 12

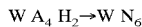

A 200 ml reactor was placed in a 0° C. water bath. To the reactor, 22.50 grams of 98% nitric acid were added and then, 11.25 grams of tris-(bis-(heptadecafluorooctylsulfonyl)imide) ytterbium (III) were added thereto while agitating with a stirrer. To the resulting solution, 1.00 gram of tetraacetylhexaazaisowurtzitane was added to prepare a mixture. The mixture was heated to 100 degrees C. and was then reacted for 3 hours. After reaction, the resultant reaction solution was dropped into 250 ml of water. The resulting mixture was left at rest to form a precipitate. The precipitate was filtered out from the mixture, washed with 250 ml of purified water and recovered by filtration from the resulting mixture. To the recovered precipitate, 50 ml of acetone were added to prepare a mixture. The mixture was stirred and was filtered to recover the tris-(bis-(heptadecafluorooctylsulfonyl)imide) ytterbium (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 17 percent yield.

The structure of the product was analyzed in the same manner as described in Example 1 and it was found that hexanitrohexaazaisowurtzitane was prepared.

Example 13

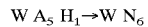

A 200 ml reactor was placed in a 0° C. water bath. To the reactor, 20.00 grams of 98% nitric acid were added and then, 10 grams of tris-(bis-(heptadecafluorooctylsulfonyl)imide) ytterbium (III) were added thereto while agitating with a stirrer. To the resulting solution, 1.00 gram of pentaacetylhexaazaisowurtzitane was added to prepare a mixture. The mixture was heated to 100 degrees C. and was then reacted for 3 hours. After reaction, the resultant reaction solution was dropped into 250 ml of water. The resulting mixture was left at rest to form a precipitate. The precipitate was filtered out, washed with 250 ml of purified water and extracted by filtration from the resulting mixture. To the recovered precipitate, 50 ml of acetone were added to obtain a mixture. The mixture was stirred and was filtered to recover the tris-(bis-(heptadecafluorooctylsulfonyl)imide) ytterbium (III). The resulting filtrate was subjected to solvent removal in an evaporator under vacuum to obtain a solid reaction product. The product was dissolved in acetonitrile and analyzed by high performance liquid chromatography. As a result, it was confirmed that hexanitrohexaazaisowurtzitane was produced in a 13 percent yield.

The structure of the product was analyzed in the same manner as described in Example 1 and it was found that hexanitrohexaazaisowurtzitane was produced.

Example 14

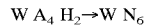

A 200 ml reactor was placed in a 0° C. water bath. To the reactor, 20.00 grams of 98% nitric acid were added and then, 4 grams of tris-(bis-(heptadecafluorooctylsulfonyl)imide) lanthanum (III) were added thereto while agitating with a stirrer. To the resulting solution, 1.00 gram of tetraacetylhexaazaisowurtzitane was added to prepare a mixture. The mixture was heated to 90 degrees C. and was then reacted for 5 hours. After reaction, the resultant reaction solution was dropped into 250 ml of water to obtain a mixture. The mixture was left at rest to form a precipitate. The precipitate was filtered out from the resulting solution, washed with 250 ml of purified water and recovered by filtration from the resulting mixture. To the recovered precipitate, 50 ml of acetone were added to obtain a mixture. The mixture was stirred and was filtered to recover the tris-(bis-(heptadecafluorooctylsulfonyl)imide)lanthanum (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 11 percent yield.

The structure of the product was analyzed in the same manner as described in Example 1 and it was found that hexanitrohexaazaisowurtzitane was produced.

Example 15

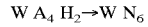

A 200 ml reactor was placed in a 0° C. water bath. To the reactor, 20.00 grams of 98% nitric acid were added and then, 8 grams of tris-(bis-(nonafluorobutylsulfonyl)imide)yttrium (III) were added thereto while agitating with a stirrer. To the resulting solution, 1.00 gram of tetraacetylhexaazaisowurtzitane was added to prepare a mixture. The mixture was heated to 100 degrees C. and was then reacted for 2 hours. After reaction, the resultant reaction solution was dropped to 250 ml of water. The resulting mixture was left at rest to form a precipitate. The precipitate was filtered out, washed with 250 ml of purified water and recovered by filtration from the resulting mixture. To the recovered precipitate, 50 ml of acetone was added to obtain a mixture. The mixture was stirred and was filtered to recover the tris-(bis-(nonafluorobutylsulfonyl)imide)lanthanum (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 16 percent yield.

The structure of the product was analyzed in the same manner as described in Example 1 and it was found that hexanitrohexaazaisowurtzitane was produced.

Example 16

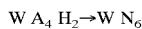

W $A_4$ $H_2$→W $N_6$

A 200 ml reactor was placed in a 0° C. water bath. To the reactor, 22.50 grams of 98% nitric acid were added and then, 11.25 grams of zeolite ZSM-5 were added thereto while agitating with a stirrer. To the resulting solution, 1.00 gram of tetraacetylhexaazaisowurtzitane was added to prepare a mixture, The mixture was heated to 100 degrees C. and was then reacted for 3 hours. After reaction, the resultant reaction solution was dropped into 250 ml of water. The resulting mixture was left at rest to form a precipitate. The precipitate was filtered out, washed with 250 ml of purified water and recovered by filtration from the resulting mixture. To the recovered precipitate, 50 ml of acetone were added to obtain a mixture. The mixture was stirred and was filtered to recover the zeolite ZSM-5. The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 15 percent yield.

The structure of the product was analyzed in the same manner as described in Example 1 and it was found that hexanitrohexaazaisowurtzitane was produced.

Example 17

W $A_5$ $H_1$→W $N_6$

A 200 ml reactor was placed in a 0° C. water bath. To the reactor, 20.00 grams of 98% nitric acid were added and 5 grams of mordenite were added thereto while agitating with a stirrer. To the resulting solution, 1.00 gram of pentaacetylhexaazaisowurtzitane was added to prepare a mixture. The mixture was heated to 100 degrees C. and was then reacted for 6 hours. After reaction, the resultant solution was dropped into 250 ml of water. The resulting mixture was left at rest to form a precipitate. The precipitate was filtered out, washed with 250 ml of purified water and recovered by filtration of the resulting mixture. To the recovered precipitate, 50 ml of acetone were added to obtain a mixture. The mixture was stirred and was filtered to recover the mordenite. The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in an 8 percent yield.

The structure of the product was analyzed in the same manner as described in Example 1 and it was found that hexanitrohexaazaisowurtzitane was produced.

Example 18

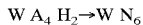

W $A_4$ $H_2$→W $N_6$

A 200 ml reactor was placed in a 0° C. water bath. To the reactor, there was added 20.00 grams of a nitric acid solution containing 10 mol % of $N_2O_5$, to which 1.00 gram of tetraacetylhexaazaisowurtzitane was added to prepare a mixture. The temperature of the mixture was raised to 100 degrees C. and then, the mixture was reacted for 3 hours. After reaction, the resulting solution was subjected to solvent evaporation to obtain a solid. The solid was neutralized with a 10% aqueous solution of $NaHCO_3$, washed with purified water and dried to recover the solid. The solid was dissolved in acetonitrile and was analyzed by high performance liquid chromatography. As a result, it was confirmed that hexanitrohexaazaisowurtzitane was produced in a 15 percent yield.

Further, the structure of the solid was analyzed in the same manner as described in Example 1 and it was found that hexanitrohexaazaisowurtzitane was produced.

Example 19

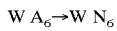

W $A_6$→W $N_6$

A 200 ml reactor was placed in a 0° C. water bath. To the reactor, 20.00 grams of a nitric acid solution containing 10 mol % of $N_2O_5$ were added and 1.00 gram of hexaacetylhexaazaisowurtzitane was then added thereto while agitating with a stirrer. The resulting mixture was heated to 100 degrees C. and was then reacted for 3 hours. After reaction, the resulting reaction solution was subjected to solvent removal to obtain a solid. The solid was neutralized with a 10% aqueous solution of $NaHCO_3$, washed with purified water and dried to recover the solid. The solid was dissolved in acetonitrile and was analyzed by high performance liquid chromatography. As a result, it was confirmed that hexanitrohexaazaisowurtzitane was produced in a 5 percent yield.

Further, the structure of the solid was analyzed in the same manner as described in Example 1 and it was found that hexanitrohexaazaisowurtzitane was produced.

Example 20

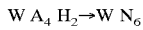

W $A_4$ $H_2$→W $N_6$

A 200 ml reactor was placed in a 0° C. water bath. To the reactor, 22.50 grams of a 98% nitric acid were added and then, 30.17 grams of polyphosphoric acid were added thereto while agitating with a stirrer. To the resultant solution, 1.00 gram of tetraacetylhexaazaisowurtzitane was added to prepare a mixture. The mixture was heated to 100 degrees C. and was then reacted for 3 hours. After reaction, the resulting solution was added to a beaker containing 250 ml ice water. The resulting mixture was agitated to dissolve a compound derived from the polyphosphoric acid and the resulting insoluble solid was extracted by filtration from the mixture, washed with water and recovered. The solid was dissolved in acetonitrile and was analyzed by high performance liquid chromatography. As a result, it was confirmed that hexanitrohexaazaisowurtzitane was produced in a 16 percent yield.

Further, the structure of the solid was analyzed in the same manner as described in Example 1 and it was found that hexanitrohexaazaisowurtzitane was produced.

Example 21

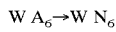

A 200 ml reactor was placed in a 0° C. water bath. To the reactor, 18.00 grams of 98% nitric acid were added and then, 24.14 grams of polyphosphoric acid were added thereto while agitating with a stirrer. To the resultant solution, 1.00 gram of hexaacetylhexaazaisowurtzitane was added to prepare a mixture. The mixture was reacted at 100 degrees C. for 3 hours. After reaction, the resulting reaction solution was added to a beaker containing 250 ml of ice water. The resulting mixture was agitated to dissolve a compound derived from the polyphosphoric acid and the insoluble solid was filtered out, washed with water and was recovered by filtration. The recovered solid was dissolved in acetonitrile and was analyzed by high performance liquid chromatography. As a result, it was confirmed that hexanitrohexaazaisowurtzitane was produced in a 9 percent yield.

Further, the structure of the solid was analyzed in the same manner as described in Example 1 and it was found that hexanitrohexaazaisowurtzitane was produced.

Example 22

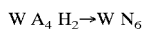

A 200 ml reactor was placed in a 0° C. water bath. To the reactor, 22.50 grams of a 98% nitric acid were added and then, 75.00 grams of trifluoroacetic anhydride were added thereto while agitating with a stirrer. To the resultant solution, 1.00 gram of tetraacetylhexaazaisowurtzitane was added to prepare a mixture. The mixture was heated to 100 degrees C. and was then reacted for 3 hours. After reaction, the resulting reaction solution was subjected to solvent removal to obtain a solid. The solid was rinsed with a 10% aqueous solution of $NaHCO_3$ and was washed with water. The solid was then dissolved in acetonitrile and was analyzed by high performance liquid chromatography. As a result, it was confirmed that hexanitrohexaazaisowurtzitane was produced in a 8 percent yield.

Further, the structure of the solid was analyzed in the same manner as described in Example 1 and it was found that hexanitrohexaazaisowurtzitane was produced.

Example 23

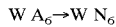

A 200 ml reactor was placed in a 0° C. water bath. To the reactor, 18.00 grams of 98% nitric acid were added and then, 60.00 grams of trifluoroacetic anhydride were added thereto while agitating with a stirrer. To the resulting solution, 1.00 gram of hexaacetylhexaazaisowurtzitane was added to prepare a mixture. The mixture was heated to 100 degrees C. and was then reacted for 3 hours. After reaction, the resulting reaction solution was subjected to solvent evaporation to obtain a solid. The solid was rinsed with a 10% aqueous solution of $NaHCO_3$ and was washed with water. The solid was then dissolved in acetonitrile and was analyzed by high performance liquid chromatography. As a result, it was confirmed that hexanitrohexaazaisowurtzitane was produced in a 3 percent yield.

Further, the structure of the solid was analyzed in the same manner as described in Example 1 and it was found that hexanitrohexaazaisowurtzitane was produced.

Example 24

A 200 ml reactor was placed in a 0° C. water bath. To the reactor, 14.92 grams of 97% sulfuric acid were added and then, 4.80 grams of 98% nitric acid were slowly dropped into it while agitating with a stirrer. To the resulting solution, 1.00 gram of dinitrosotetraacetylhexaazaisowurtzitane was added to prepare a mixture. The mixture was heated to 60 degrees C. and was then reacted for 24 hours. After reaction, the resultant reaction solution was dropped into 250 grams of ice water. The resulting mixture was left at rest and was then filtered to obtain a solid. The solid was washed with 250 grams of purified water to obtain 1.09 gram of hexanitrohexaazaisowurtzitane in a 98 percent yield.

As a result of structural analysis of the solid in the same manner as described in Example 1, it was found that hexanitrohexaazaisowurtzitane was produced.

Example 25

A 200 ml reactor was placed in a 0° C. water bath. To the reactor, 14.45 grams of 97% sulfuric acid were added and then, 4.64 grams of 98% nitric acid were slowly dropped thereinto while agitating with a stirrer. To the resulting solution, 1.00 gram of mononitrosopentaacetylhexaazaisowurtzitane was added to prepare a mixture. The temperature of the mixture was elevated to 60 degrees C. and then, the mixture was reacted for 24 hours. After reaction, the resultant reaction solution was added to 250 grams of ice water to prepare a mixture. The mixture was left at rest and was then filtered to obtain a solid, which was washed with 250 grams of purified water to obtain 1.08 gram of hexanitrohexaazaisowurtzitane in a 98 percent yield.

As a result of structural analysis of the solid in the same manner as described in Example 1, it was found that hexanitrohexaazaisowurtzitane was produced.

Example 26

A 200 ml reactor was placed in a 0° C. water bath. To the reactor, 18.58 grams of 98% nitric acid were added and then, 8.40 grams of trifluoroacetic acid were added thereto while agitating with a stirrer. To the resulting solution, 1.00 gram of mononitrosopentaacetylhexaazaisowurtzitane was added to prepare a mixture. The temperature of the mixture was elevated to 100 degrees C. and the mixture was then reacted for 3 hours. After reaction, the resulting reaction solution was subjected to solvent evaporation to obtain a solid. The solid was neutralized with a 10% aqueous solution of $NaHCO_3$ and was extracted by filtration from the resulting mixture. The extracted solid was washed with water, dried, dissolved in acetonitrile and analyzed by high performance liquid chromatography. As a result, it was confirmed that hexanitrohexaazaisowurtzitane was produced in a 8 percent yield.

Further, the structure of the solid was analyzed in the same manner as described in Example 1 and it was found that hexanitrohexaazaisowurtzitane was produced.

Example 27

A 200 ml reactor was placed in a 0° C. water bath. To the reactor, 19.19 grams of 98% nitric acid were added and then, 10.80 grams of diphosphorus pentoxide were added thereto while agitating with a stirrer. To the resulting solution, 1.00 gram of dinitrosotetraacetylhexaazaisowurtzitane was added to prepare a mixture. The mixture was heated to 100 degrees C. and was then reacted for 3 hours. After reaction, the resulting reaction solution was subjected to solvent removal, followed by addition of 20 ml of water and filtration to obtain a solid. The solid was neutralized with a 10% aqueous solution of $NaHCO_3$ and was recovered by filtration from the resulting mixture. The recovered solid was washed with water, dried, dissolved in acetonitrile and analyzed by high performance liquid chromatography. As a result, it was confirmed that hexanitrohexaazaisowurtzitane was produced in a 7 percent yield.

Further, the structure of the solid was analyzed in the same manner as described in Example 1 and it was found that hexanitrohexaazaisowurtzitane was produced.

Example 28

A 200 ml reactor was placed in a 0° C. water bath. To the reactor, 19.19 grams of 98% nitric acid were added and then, 25.73 grams of polyphosphoric acid were added thereto while agitating with a stirrer. To the resulting solution, 1.00 gram of dinitrosotetraaacetylhexaazaisowurtzitane was added to prepare a mixture. The temperature of the mixture was raised to 100 degrees C. and the mixture was then reacted for 3 hours. After reaction, the resulting reaction solution was added to a beaker containing 20 ml of water. The resulting mixture was agitated and was filtered to obtain an insoluble solid. The solid was washed with water, dried, dissolved in acetonitrile and analyzed by high performance liquid chromatography. As a result, it was confirmed that hexanitrohexaazaisowurtzitane was produced in a 11 percent yield.

Further, the structure of the solid was analyzed in the same manner as described in Example 1 and it was found that hexanitrohexaazaisowurtzitane was produced.

Example 29

A 200 ml reactor was placed in a 0° C. water bath. To the reactor, 19.19 grams of 98% nitric acid were added and then, 63.96 grams of trifluoroacetic anhydride were added thereto while agitating with a stirrer. To the resulting solution, 1.00 gram of mononitrosopentaacetylhexaazaisowurtzitane was added to prepare a mixture. The temperature of the mixture was raised to 100 degrees C. and the mixture was then reacted for 3 hours. After reaction, the resulting reaction solution was subjected to solvent removal to obtain a solid. The solid was washed with a 10% aqueous solution of $NaHCO_3$ and water, dried, dissolved in acetonitrile and analyzed by high performance liquid chromatography. As a result, it was confirmed that hexanitrohexaazaisowurtzitane was produced in a 2 percent yield.

Further, the structure of the solid was analyzed in the same manner as described in Example 1 and it was found that hexanitrohexaazaisowurtzitane was produced.

Example 30

A 200 ml reactor was placed in a 0° C. water bath. To the reactor, 20.00 grams of a nitric acid solution containing 10 mol % of $N_2O_5$ were added and 1.00 gram of mononitrosopentaacetylhexaazaisowurtzitane was then added thereto while agitating with a stirrer. The resulting mixture was heated to 100 degrees C. and was then reacted for 3 hours. After reaction, the resulting reaction solution was subjected to solvent evaporation to obtain a solid. The solid was neutralized with a 10% aqueous solution of $NaHCO_3$, washed with purified water and dried to recover the solid. The recovered solid was dissolved in acetonitrile and was analyzed by high performance liquid chromatography. As a result, it was confirmed that hexanitrohexaazaisowurtzitane was produced in a 5 percent yield.

Further, the structure of the solid was analyzed in the same manner as described in Example 1 and it was found that hexanitrohexaazaisowurtzitane was produced.

Example 31

A 200 ml reactor was placed in a 0° C. water bath. To the reactor, 9.59 grams of 98% nitric acid were added and 6.09 grams of sulfuric anhydride were added thereto while agitating with a stirrer. To the resulting solution, 1.00 gram of dinitrosotetraacetylhexaazaisowurtzitane was added to prepare a mixture. The temperature of the mixture was raised to 60 degrees C. and the mixture was then reacted for 24 hours. After reaction, the resultant reaction solution was added to 250 grams of ice water. The resulting mixture was left at rest and was filtrated through a membrane filter to obtain a solid. The solid was washed with 250 grams of purified water to obtain 1.10 gram of hexanitrohexaazaisowurtzitane in a 99 percent yield.

As a result of structural analysis of the solid in the same manner as described in Example 1, it was found that hexanitrohexaazaisowurtzitane was produced.

Example 32

A 200 ml reactor was placed in a 0° C. water bath. To the reactor, 18.58 grams of 98% nitric acid were added and 9.29 grams of Nafion-NR50 were added thereto while agitating with a stirrer. To the resulting solution, 1.00 gram of mononitrosopentaacetylhexaazaisowurtzitane was added to obtain a mixture. The mixture was heated to 100 degrees C. and was then reacted for 3 hours. After reaction, the resultant reaction solution was dropped into 250 ml of water, followed by being left at rest to form a precipitate. The precipitate was filtered out from the resulting mixture, washed with 250 ml of purified water and recovered by filtration. To the recovered precipitate, 50 ml of acetone were added and stirred to prepare a mixture. The mixture was filtered to recover the Nafion-NR50. The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 49 percent yield.

Further, the structure of the product was analyzed in the same manner as described in Example 1 and it was found that hexanitrohexaazaisowurtzitane was produced.

Example 33

A 200 ml reactor was placed in a 0° C. water bath. To the reactor, 18.58 grams of 98% nitric acid were added and 9.29 grams of tris-(bis-(heptadecafluorooctylsulfonyl)imide) yttrium (III) were then added thereto while agitating with a stirrer. To the resulting solution, 1.00 gram of dinitrosotetraacetylhexaazaisowurtzitane was added to prepare a mixture. The temperature of the mixture was elevated to 100 degrees C. and the mixture was then reacted for 3 hours. After reaction, the resultant reaction solution was dropped into 250 ml of water and left at rest to form a precipitate. A precipitate was obtained by filtration from the resulting mixture, washed with 250 ml of purified water and recovered by filtration. To the recovered precipitate, 50 ml of acetone were added to obtain a mixture. The mixture was stirred and was filtered to recover the tris-(bis-(heptadecafluorooctylsulfonyl)imide) yttrium (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 10 percent yield.

The structure of the product was analyzed in the same manner as described in Example 1 and it was found that hexanitrohexaazaisowurtzitane was produced.

Example 34

$W\ A_4\ NS_2 \rightarrow W\ N_6$

A 200 ml reactor was placed in a 0° C. water bath. To the reactor, 18.58 grams of 98% nitric acid were added and 3.29 grams of tris-(bis-(heptadecafluorooctylsulfonyl)imide) europium (III) were then added thereto while agitating with a stirrer. To the resulting solution, 1.00 gram of dinitrosotetraacetylhexaazaisowurtzitane was added to prepare a mixture. The temperature of the mixture was elevated to 100 degrees C. and the mixture was then reacted for 8 hours. After reaction, the resultant reaction solution was dropped into 250 ml of water, followed by being left at rest to form a precipitate. The precipitate was filtered out from the resulting mixture, washed with 250 ml of purified water and recovered by filtration. To the recovered precipitate, 50 ml of acetone were added to obtain a mixture. The mixture was stirred and was filtered to recover the tris-(bis-(heptadecafluorooctylsulfonyl)imide)europium (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in a 6 percent yield.

Further, the structure of the product was analyzed in the same manner as described in Example 1, it was found that hexanitrohexaazaisowurtzitane was produced.

Example 35

$W\ A_4\ NS_2 \rightarrow W\ N_6$

A 200 ml reactor was placed in a 0° C. water bath. To the reactor, 18.58 grams of 98% nitric acid were added and 4.29 grams of tris-(bis-(nonafluorobutylsulfonyl)imide)ytterbium (III) were then added thereto while agitating with a stirrer. To the resulting solution, 1.00 gram of dinitrosotetraacetylhexaazaisowurtzitane was added to prepare a mixture. The temperature of the mixture was elevated to 90 degrees C. and the mixture was then reacted for 4 hours. After reaction, the resultant reaction solution was dropped into 250 ml of water. The resulting mixture was left at rest to form a precipitate. The precipitate was filtered out from the mixture, washed with 250 ml of purified water and recovered by filtration from the resulting mixture. To the recovered precipitate, 50 ml of acetone were added to obtain a mixture. The mixture was stirred and was filtered to recover the tris-(bis-(nonafluoro-butylsulfonyl) imide) ytterbium (III). The resulting filtrate was subjected to solvent removal in an evaporator under vacuum to obtain a solid reaction product. The product was dissolved in acetonitrile and analyzed by high performance liquid chromatography. As a result, it was confirmed that hexanitrohexaazaisowurtzitane was produced in an 18 percent yield.

Further, the structure of the product was analyzed in the same manner as described in Example 1 and it was found that hexanitrohexaazaisowurtzitane was produced.

Example 36

$W\ A_4\ N_2 \rightarrow W\ N_6$

A 200 ml reactor was placed in a 0° C. water bath. To the reactor, 13.80 grams of 97% sulfuric acid were added and then, 4.44 grams of 98% nitric acid were slowly dropped thereto while agitating with a stirrer. To the resulting solution, 1.00 gram of dinitrosotetraacetylhexaazaisowurtzitane was added to prepare a mixture. The mixture was heated to 60 degrees C. and was then reacted for 24 hours. After reaction, the resultant reaction solution was added to 250 grams of ice water. The resulting mixture was left at rest and was filtrated through a membrane filter to obtain a solid. The solid was washed with 250 grams of purified water to obtain 1.01 grams of hexanitrohexaazaisowurtzitane in a 98 percent yield.

As a result of structural analysis of the solid in the same manner as described in Example 1, it was found that hexanitrohexaazaisowurtzitane was produced.

Example 37

$W\ A_5\ N_1 \rightarrow W\ N_6$

A 200 ml reactor was placed in a 0° C. water bath. To the reactor, 13.81 grams of 97% sulfuric acid were added and then, 4.46 grams of 98% nitric acid were slowly dropped thereinto while agitating with a stirrer. To the resulting solution, 1.00 gram of mononitropentaacetylhexaazaisowurtzitane was added to prepare a mixture. The mixture was heated to 60 degrees C. and was then reacted for 24 hours. After reaction, the resultant reaction solution was added to 250 grams of ice water. The resulting mixture was left at rest and was filtered through a membrane filter to extract a solid, which was washed with 250 grams of purified water to obtain 1.05 gram of hexanitrohexaazaisowurtzitane in a 98 percent yield.

As a result of structural analysis of the solid in the same manner as described in Example 1, it was found that hexanitrohexaazaisowurtzitane was produced.

Example 38

$W\ A_5\ N_1 \rightarrow W\ N_6$

A 200 ml reactor was placed in a 0° C. water bath. To the reactor, 17.87 grams of 98% nitric acid were added and 8.09 grams of trifluoroacetic acid were then added thereto while agitating with a stirrer. To the resulting solution, 1.00 gram of mononitropentaacetylhexaazaisowurtzitane was added to prepare a mixture. The temperature of the mixture was raised to 100 degrees C. and the mixture was then reacted for 3 hours. After reaction, the resulting reaction solution was subjected to solvent evaporation to obtain a solid. The solid was neutralized with a 10% aqueous solution of $NaHCO_3$ and was recovered by filtration from the resulting mixture. The recovered solid was washed with water, dried, dissolved in acetonitrile and analyzed by high performance liquid chromatography. As a result, it was confirmed that hexanitrohexaazaisowurtzitane was produced in a 6 percent yield.

Further, the structure of the solid was analyzed in the same manner as described in Example 1 and it was found that hexanitrohexaazaisowurtzitane was produced.

Example 39

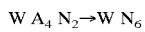

A 200 ml reactor was placed in a 0° C. water bath. To the reactor, 17.75 grams of 98% nitric acid were added and 10.00 grams of diphosphorus pentoxide were then added thereto while agitating with a stirrer. To the resulting solution, 1.00 gram of dinitrosotetraacetylhexaazaisowurtzitane was added to prepare a mixture. The temperature of the mixture was elevated to 100 degrees C. and the mixture was then reacted for 3 hours. After reaction, the resulting reaction solution was subjected to solvent evaporation, followed by addition of 20 ml of water and filtration to obtain a solid. The solid was neutralized with a 10% aqueous solution of $NaHCO_3$. The resulting mixture was filtered to recover the solid. The solid was washed with water, dried, dissolved in acetonitrile and was analyzed by high performance liquid chromatography. As a result, it was confirmed that hexanitrohexaazaisowurtzitane was produced in a 9 percent yield.

Further, the structure of the solid was analyzed in the same manner as described in Example 1 and it was found that hexanitrohexaazaisowurtzitane was produced.

Example 40

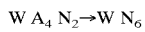

A 200 ml reactor was placed in a 0° C. water bath. To the reactor, 17.75 grams of 98% nitric acid were added and 23.80 grams of polyphosphoric acid were then added thereto while agitating with a stirrer. To the resultant solution, 1.00 gram of dinitrosotetraacetylhexaazaisowurtzitane was added to prepare a mixture. The mixture was heated to 100 degrees C. and was then reacted for 3 hours. After reaction, the resulting reaction solution was added to a beaker containing 20 ml of water. The resulting mixture was agitated and was filtered out an insoluble solid. The solid was washed with water, dried, dissolved in acetonitrile and analyzed by high performance liquid chromatography. As a result, it was confirmed that hexanitrohexaazaisowurtzitane was produced in a 12 percent yield.

Further, the structure of the solid was analyzed in the same manner as described in Example 1 and it was found that hexanitrohexaazaisowurtzitane was produced.

Example 41

A 200 ml reactor was placed in a 0° C. water bath. To the reactor, 17.75 grams of 98% nitric acid were added and 59.57 grams of trifluoroacetic anhydride were then added thereto while agitating with a stirrer. To the resulting solution, 1.00 gram of mononitropentaacetylhexaazaisowurtzitane was added to prepare a mixture. The temperature of the mixture was elevated to 100 degrees C. and the mixture was then reacted for 3 hours. After reaction, the resulting reaction solution was subjected to solvent evaporation to obtain a solid. The solid was washed with a 10% aqueous solution of $NaHCO_3$ and water, dried, dissolved in acetonitrile and analyzed by high performance liquid chromatography. As a result, it was confirmed that hexanitrohexaazaisowurtzitane was produced in a 3 percent yield.

Further, the structure of the solid was analyzed in the same manner as described in Example 1 and it was found that hexanitrohexaazaisowurtzitane was produced.

Example 42

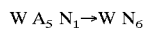

A 200 ml reactor was placed in a 0° C. water bath. To the reactor, 20.00 grams of a nitric acid solution containing 10 mol % of $N_2O_5$ were added and 1.00 gram of mononitropentaacetylhexaazaisowurtzitane was then added thereto while agitating with a stirrer. The temperature of the resulting mixture was elevated to 100 degrees C. and the mixture was then reacted for 3 hours. After reaction, the resulting reaction solution was subjected to solvent removal to obtain a solid. The solid was neutralized with a 10% aqueous solution of $NaHCO_3$, washed with purified water and dried to recover the solid. The solid was dissolved in acetonitrile and was analyzed by high performance liquid chromatography. As a result, it was confirmed that hexanitrohexaazaisowurtzitane was produced in a 6 percent yield.

Further, the structure of the solid was analyzed in the same manner as described in Example 1 and it was found that hexanitrohexaazaisowurtzitane was produced.

Example 43

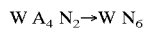

A 200 ml reactor was placed in a 0° C. water bath. To the reactor, 8.94 grams of 98% nitric acid were added and then, 5.67 grams of sulfuric anhydride were added thereto while agitating with a stirrer. To the resulting solution, 1.00 gram of dinitrosotetraacetylhexaazaisowurtzitane was added to prepare a mixture. The mixture was heated to 60 degrees C. and was then reacted for 24 hours. After reaction, the resultant reaction solution was added to 250 grams of ice water, followed by being left at rest. The resulting mixture was left at rest and was filtered to extract a solid, which was washed with 250 grams of purified water to obtain 1.06 grams of hexanitrohexaazaisowurtzitane in a 99 percent yield.

As a result of structural analysis of the solid in the same manner as described in Example 1, it was found that hexanitrohexaazaisowurtzitane was produced.

Example 44

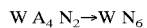

A 200 ml reactor was placed in a 0° C. water bath. To the reactor, 17.87 grams of 98% nitric acid were added and 8.94 grams of Nafion-NR50 were then added thereto while agitating with a stirrer. To the resulting solution, 1.00 gram of dinitrosotetraacetylhexaazaisowurtzitane was added to prepare a mixture. The temperature of the mixture was elevated to 100 degrees C. and the mixture was then reacted for 3 hours. After reaction, the resultant reaction solution was dropped into 250 ml of water. The resulting mixture was left at rest to form a precipitate. The precipitate was filtered out from the mixture, washed with 250 ml of purified water and recovered by filtration from the resulting mixture. After the recovered precipitate was added to 50 ml of acetone, the resulting mixture was stirred and was filtered to recover the Nafion-NR50. The resulting filtrate was subjected to solvent removal in an evaporator under vacuum to obtain a solid reaction product. The product was dissolved in acetonitrile and was analyzed by the high performance liquid chromatography. As a result, it was confirmed that hexanitrohexaazaisowurtzitane was produced in a 68 percent yield.

Further, the structure of the product was analyzed in the same manner as described in Example 1 and it was found that hexanitrohexaazaisowurtzitane was produced.

Example 45

A 200 ml reactor was placed in a 0° C. water bath. To the reactor, 17.75 grams of 98% nitric acid were added and 8.87 grams of tris-(bis-(heptadecafluorooctylsulfonyl)imide) ytterbium (III) were then added thereto while agitating with a stirrer. To the resulting solution, 1.00 gram of dinitrosotetraacetylhexaazaisowurtzitane was added to prepare a mixture. The temperature of the mixture was elevated to 100 degrees C. and the mixture was then reacted for 3 hours. After reaction, the resultant reaction solution was dropped to 250 ml of water. The resulting mixture was left at rest to form a precipitate. The precipitate was filtered out from the mixture, washed with 250 ml of purified water and recovered by filtration. The recovered precipitate was added to 50 ml of acetone to obtain a mixture, The mixture was stirred and was filtered to recover the tris-(bis-(heptadecafluorooctylsulfonyl)imide) ytterbium (III). The resulting filtrate was subjected to solvent removal in an evaporator under vacuum to obtain a solid reaction product. The product was dissolved in acetonitrile and was analyzed by the high performance liquid chromatography. As a result, it was confirmed that hexanitrohexaazaisowurtzitane was produced in a 18 percent yield.

The structure of the product was analyzed in the same manner as described in Example 1 and it was found that hexanitrohexaazaisowurtzitane was produced.

Example 46

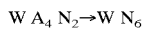

A 200 ml reactor was placed in a 0° C. water bath. To the reactor, 17.75 grams of 98% nitric acid were added and 4.57 grams of tris-(bis-(heptadecafluorooctylsulfonyl)imide) samarium (III) were then added thereto while agitating with a stirrer. To the resulting solution, 1.00 gram of dinitrosotetraacetylhexaazaisowurtzitane was added to prepare a mixture. The mixture was heated to 100 degrees C. and the mixture was then reacted for 3 hours. After reaction, the resultant reaction solution was dropped to 250 ml of water. The resulting mixture was left at rest to form a precipitate. The precipitate was filtered out from the mixture, washed with 250 ml of purified water and recovered by filtration. The recovered precipitate was added to 50 ml of acetone to obtain a mixture. The mixture was stirred and was filtered to recover the tris-(bis-(heptadecafluorooctylsulfonyl)imide) samarium (III). The resulting filtrate was subjected to solvent removal in an evaporator under vacuum to obtain a solid reaction product. The product was dissolved in acetonitrile and was analyzed by high performance liquid chromatography. As a result, it was confirmed that hexanitrohexaazaisowurtzitane was produced in an 8 percent yield.

The structure of the product was analyzed in the same manner as described in Example 1 and it was found that hexanitrohexaazaisowurtzitane was produced.

Example 47

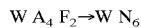

A 200 ml reactor was placed in a 0° C. water bath. To the reactor, 7.50 grams of 97% sulfuric acid were added and then, 24.11 grams of 98% nitric acid were slowly dropped thereinto while agitating with a stirrer. To the resulting solution, 1.00 gram of diformyltetraacetylhexaazaisowurtzitane was added to obtain a mixture. The mixture was heated to 100 degrees C. and was then reacted for 15 hours. After reaction, the resultant reaction solution was added to 250 grams of ice water. The resulting mixture was left at rest and was filtrated through a membrane filter to obtain a solid, which was washed with 250 grams of purified water to obtain 0.87 gram of hexanitrohexaazaisowurtzitane in a 78 percent yield.

As a result of structural analysis of the solid in the same manner as described in Example 1, it was found that hexanitrohexaazaisowurtzitane was produced.

Example 48

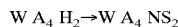

To a 200 ml reactor, 3.36 grams of tetraacetylhexaazaisowurtzitane and 100 ml of 50% acetic acid were added to obtain a mixture, to which 20 ml of a 4M aqueous sodium nitrite solution were slowly dropped under agitation at 0 degree C. The resulting mixture was heated to 30 degrees C. and was then reacted for 4 hours. To the rsulting reaction solution, 500 ml of chloroform were added. The resulting solution was vigorously agitated and was left at rest. The resulting organic phase separated from the solution was subjected to solvent evaporation. As a result, it was confirmed that 3.73 grams of dinitrosotetraacetylhexaazaisowurtzitane were obtained as a product in a 95 percent yield. Results of structural analysis of the product are as follows.

The $^1$HNMR spectrum of the product (solvent: $CDCl_3$, TMS: standard reference compound and δ: dimensionless quantity of chemical shift in ppm) showed peaks respectively at 2.05 (s, 6H, $COCH_3$), 2.17 (s, 6H, $COCH_3$), 5.46 (m, 2H, CH), 6.62 (m, 2H, CH), 7.30 (s, 2H, CH), by which 4 acetyl groups and 6 methine groups of the W skeleton were confirmed.

As a result of IR absorption spectroscopy of the product, there were confirmed an IR absorption in the vicinity of 1,670 $cm^{-1}$ ascribed to the carbonyl groups (C=O) of acetyl groups and two IR absorptions in the vicinities of 1,380 $cm^{-1}$ and 1,350 $cm^{-1}$ ascribed to nitroso groups.

Incidentally, two absorptions in the region between 3,300 $cm^{-1}$ and 3,400 $cm^{-1}$ were entirely vanished which were ascribed to the NH groups of tetraacetylhexaazaisowurtzitane.

Example 49

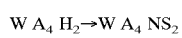

To a 200 ml reactor, 3.36 grams of tetraacetylhexaazaisowurtzitane and 100 ml of 35% hydrochloric acid were added, which were cooled down to 0 degree C. To the resulting mixture, 20 ml of a 4M aqueous sodium nitrite solution were slowly dropped under agitation at 0 degree C.

The resulting mixture was heated to 30 degrees C., then agitated for 4 hours. To the resulting reaction solution, 500 ml of chloroform were added. The resulting solution was vigorously agitated and was left at rest. The resulting organic phase separated from the solution was subjected to solvent evaporation. As a result, it was confirmed that 3.49 grams of dinitrosotetraacetylhexaazaisowurtzitane was obtained as a product in a 89 percent yield.

The structure of the product was analyzed in the same manner as described in Example 48 and it was found that dinitrosotetraacetylhexaazaisowurtzitane was produced.

Example 50

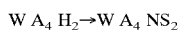

To a 200 ml reactor, 3.36 grams of tetraacetylhexaazaisowurtzitane and 100 ml of acetic acid were added and were cooled down to 0 degree C. Into the resulting reaction solution, about 20 grams of dinitrogen tetroxide gas were slowly blown under agitation at 0 degree C., followed by agitation for 1 hour at 0 degree C. After reaction, the resulting reaction solution was subjected to solvent evaporation under vacuum to obtain a solid, which was washed with water and was dried. As a result, it was confirmed that 3.73 grams of dinitrosotetraacetylhexaazaisowurtzitane were obtained as a product in a 95 percent yield.

As a result of structural analysis of the product in the same manner as described in Example 48, it was found that dinitrosotetraacetylhexaazaisowurtzitane was produced.

Example 51

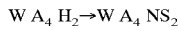

To a 200 ml reactor, 3.36 grams of tetraacetylhexaazaisowurtzitane and 100 ml of pyridine were added and were cooled down to 0 degree C. To the resulting solution, 10 ml of a 4.8 M acetic anhydride solution of nitrosyl chloride were slowly dropped under agitation at 0 degree C., followed by one-hour of agitation. After reaction, the resulting reaction solution was added to 100 grams of ice water to form a precipitate. The resulting precipitate was filtered out, washed with water and dried, and it was confirmed that 2.75 grams of dinitrosotetraacetylhexaazaisowurtzitane were obtained as a product in a 70 percent yield.

As a result of structural analysis of the product in the same manner as described in Example 48, it was found that dinitrosotetraacetylhexaazaisowurtzitane was produced.

Example 52

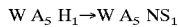

To a 200 ml reactor, 3.78 grams of pentaaacetylhexaazaisowurtzitane and 100 ml of 50% acetic acid were added and were cooled down to 0 degree C. To the resulting mixture, 20 ml of a 4M sodium nitrite solution were slowly dropped under agitation at 0 degree C. The resulting mixture was heated to 30 degrees C. and was then agitated for 4 hours. To the resulting reaction solution, 500 ml of chloroform was added. The resulting solution was vigorously agitated and was left at rest. The resulting organic phase separated from the solution was subjected to solvent evaporation under vacuum. As a result, it was confirmed that 3.79 grams of mononitrosopentaaacetylhexaazaisowurtzitane were obtained as a product in a 93 percent yield.

The structure of the product was analyzed in the same manner as described in Example 48 and it was found that mononitrosopentaacetylhexaazaisowurtzitane was produced.

Example 53

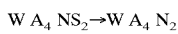

To a 100 ml reactor, 20.00 grams of 98% nitric acid were added and 0.93 gram of dinitrosotetraacetyl-hexaazaisowurtzitane were then added thereto. The resulting mixture was reacted for 5 hours at room temperature. After reaction, the nitric acid was evaporated from the resulting reaction solution under vacuum, followed by washing with water and drying. As a result, it was confirmed that 0.96 gram of dinitrosotetraacetylhexaazaisowurtzitane was obtained as a product in a 95 percent yield. Results of structural analysis of the product are as follows.

The $^1$HNMR spectrum of the product (solvent: DMSO-$d_6$, TMS: standard reference compound and δ: dimensionless quantity of chemical shift in ppm) showed peaks at 2.10 (s, 12H, COCH$_3$), 6.75 (m, 2H, CH) and 7.35 (4H, CH having a singlet peak at 7.35 ppm with shoulder peaks on a low magnetic field side).

As a result of measuring the IR spectrum of the product, there were confirmed an IR absorption in the vicinity of 1,680 cm$^{-1}$ [1] ascribed to the stretching vibration of carbonyl groups (C=O) of acetyl groups and two IR absorption in the vicinities of 1,570 cm$^{-1}$ and 1,300 cm$^{-1}$ ascribed to the stretching vibration of nitro groups, from which there was learned the presence of nitro and acetyl groups in the product.

The EI-mass spectrum of the product showed a parent ion peak of m/z 426.

As a result of measuring the decomposition temperature of the product at a heating rate of 10 degrees C./min., its peak temperature was 314 degrees C.

Example 54

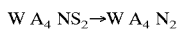

A 200 ml reactor was placed in a 0° C. water bath. To the reactor, 20 ml of N$_2$O$_4$ were added and 0.4 gram of dinitrosotetraacetylhexaazaisowurtzitane were then added thereto. The resulting mixture was reacted at 10 degrees C. for 5 hours. After reaction, the resulting reaction solution was subjected to solvent evaporation to obtain a solid. The solid was neutralized with a 10% aqueous solution of NaHCO$_3$ and was washed with water. As a result, it was confirmed that dinitrosotetraacetylhexaazaisowurtzitane was obtained as a product in a 92 percent yield.

Further, the structure of the product was analyzed in the same manner as described in Example 53 and it was found that dinitrosotetraacetylhexaazaisowurtzitane was produced.

Example 55

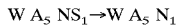

A 200 ml reactor was placed in a 0° C. water bath. To the reactor, 30 ml of 97% nitric acid were added and 0.96 gram of mononitrosopentaacetylhexaazaisowurtzitane were then added thereto. The resulting mixture was reacted at room temperature for 5 hours. After reaction, the resulting reaction solution was subjected to solvent evaporation to obtain a solid product. The product was washed with water and was dried. As a result, it was confirmed that mononitropentraacetylhexaazaisowurtzitane was produced in a 90 percent yield.

Further, the structure of the product was analyzed in the same manner as described in Example 53 and it was found that mononitropentraacetylhexaazaisowurtzitane was produced.

Example 56

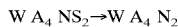

A 200 ml reactor was placed in a 0° C. water bath. To the reactor, 81 grams of 97% sulfuric acid were added and then, 22.5 grams of 97% nitric acid were slowly dropped thereto while agitating with a stirrer. To the resulting solution, 0.4 gram of dinitrosotetraacetylhexaazaisowurtzitane was added to obtain a mixture. The mixture was stirred at 20 degrees C. for 30 minutes. After reaction, the resultant reaction solution was left at rest to precipitate a white solid. The resulting supernatant liquid phase was removed from the solution and 20 grams of ice was added to the rest of the solution, followed by filtration. The resulting solid was washed with a 10% aqueous solution of $NaHCO_3$ and purified water, dried, dissolved in acetonitrile and analyzed by high performance liquid chromatography. As a result, it was confirmed that dinitro-tetraacetylhexaazaisowurtzitane was produced in a 20 percent yield.

Further, the structure of the solid was analyzed in the same manner as described in Example 53 and it was found that dinitrotetraaceylhexaazaisowurtzitane was produced.

Example 57

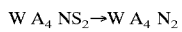

A 200 ml reactor was placed in a 0° C. water bath. To the reactor, 6.95 grams of a nitric acid solution containing 10 mol % of $N_2O_5$ were added and 1.00 gram of dinitrosotetraacetylhexaazaisowurtzitane was then added thereto while agitating with a stirrer. The resulting mixture was reacted at 25 degrees C. for one hour. After reaction, the resulting reaction solution was subjected to solvent evaporation to obtain a solid. The solid was neutralized with a 10% aqueous solution of $NaHCO_3$ and was recovered by filtration from the resulting mixture. The recovered solid was washed with water, dried, dissolved in acetonitrile and analyzed by high performance liquid chromatography. As a result, it was confirmed that dinitro-tetraacetylhexaazaisowurtzitane was produced in a 70 percent yield.

Further, the structure of the solid was analyzed in the same manner as described in Example 53 and it was found that dinitrosotetraacetylhexaazaisowurtzitane was produced.

Example 58

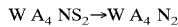

A 200 ml reactor was placed in a 0° C. water bath. To the reactor, 18.22 grams of 97% nitric acid were added and 5.21 grams of trifluoroacetic acid were then added thereto while agitating with a stirrer. To the resulting solution, 0.4 gram of dinitrosotetraacetylhexaazaisowurtzitane were added and the resulting mixture was reacted at 60 degrees C. for one hour. After reaction, the resulting reaction solution was subjected to solvent evaporation to obtain a solid. The solid was neutralized with a 10% aqueous solution of $NaHCO_3$ and was recovered by filtration from the resulting mixture. The recovered solid was washed with water, dried, dissolved in acetonitrile and analyzed by high performance liquid chromatography. As a result, it was confirmed that dinitro-tetraacetylhexaazaisowurtzitane was produced in a 42 percent yield.

Further, the structure of the solid was analyzed in the same manner as described in Example 53 and it was found that dinitrosotetraacetylhexaazaisowurtzitane was produced.

Example 59

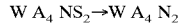

A 200 ml reactor was placed in a 0° C. water bath. To the reactor, 17.64 grams of 97% nitric acid were added and 3.98 grams of diphosphorus pentoxide were then added thereto while agitating with a stirrer. To the resulting solution, 0.4 gram of dinitrosotetraacetylhexaazaisowurtzitane were added to obtain a mixture. The mixture was agitated at 30 degrees C. for 30 minutes. After reaction, the resulting reaction solution was subjected to solvent evaporation, followed by addition of 20 ml of water and filtration to obtain a solid. The solid was washed with water, dried, dissolved in acetonitrile and analyzed by high performance liquid chromatography. As a result, it was confirmed that dinitrosotetraacetylhexaazaisowurtzitane was produced in a 56 percent yield.

Further, the structure of the solid was analyzed in the same manner as described in Example 53 and it was found that dinitrosotetraacetylhexaazaisowurtzitane was produced.

Example 60

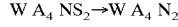

20.16 grams of 97% nitric acid were added and 44.33 grams of polyphosphoric acid were then added while agitating with a stirrer. To the resultant solution, 0.4 gram of dinitrosotetraacetylhexaazaisowurtzitane were added. The resulting mixture was reacted at 40 degrees C. for 40 minutes. After reaction, the resulting reaction solution was added to a beaker containing 20 ml of water. The resulting mixture was agitated and was filtered to obtain an insoluble solid. The solid was washed with water, dried, dissolved in acetonitrile and analyzed by high performance liquid chromatography. As a result, it was confirmed that dinitrosotetraacetylhexaazaisowurtzitane was produced in a 56 percent yield.

Further, the structure of the solid was analyzed in the same manner as described in Example 53 and it was found that dinitroteteraacetylhexaazaisowurtzitane was produced.

Example 61

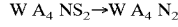

A 200 ml reactor was placed in a 0° C. water bath. To the reactor, 18.22 grams of 97% nitric acid were added and 60.73 grams of trifluoroacetic anhydride were then added thereto while agitating with a stirrer. To the resulting solution, 0.4 gram of dinitrosotetraacetylhexaazaisowurtzitane were added to obtain a mixture. The mixture was reacted at 30 degrees C. for one hour. After reaction, the resulting reaction solution was subjected to solvent evaporation to obtain a solid. The solid was neutralized with a 10% aqueous solution of $NaHCO_3$ washed with water, dried dissolved in acetonitrile and analyzed by high performance liquid chromatography. As a result, it was confirmed that dinitrosotetraacetylhexaazaisowurtzitane was produced in a 72 percent yield.

Further, the structure of the solid was analyzed in the same manner as described in Example 53 and it was found that dinitrosotetraacetylhexaazaisowurtzitane was produced.

Example 62

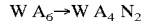

A 200 ml reactor was placed in a 0° C. water bath. To the reactor, 20 grams of a nitric acid solution containing 10 mol % of $N_2O_5$ were added and 0.4 gram of hexaacetylhexaazaisowurtzitane were then added thereto. The resulting mixture was reacted at 60 degrees C. for 8 hours. After reaction, organic components were extracted from the resulting reaction solution four times by using chloroform in portions of 200 ml. From the resulting mixture, the chloroform was evaporated under vacuum to obtain a solid. The solid was washed with a 10% aqueous solution of $NaHCO_3$ to obtain a mixture of various nitro compounds. The mixture was dissolved in acetonitrile and was analyzed by high performance liquid chromatography. As a result, it was confirmed that dinitrosotetraacetylhexaazaisowurtzitane was produced as a major component in a 43 percent yield.

Further, the structure of the component was analyzed in the same manner as described in Example 53 and it was found that dinitrosotetraacetylhexaazaisowurtzitane was produced.

Example 63

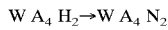
$W\ A_4\ H_2 \rightarrow W\ A_4\ N_2$

A 200 ml reactor was placed in a 0° C. water bath. To the reactor, 20 grams of a nitric acid solution containing 10 mol % of $N_2O_5$ were added and 0.4 gram of tetraacetylhexaazaisowurtzitane were then added thereto. The resulting mixture was reacted at 60 degrees C. for 8 hours. After reaction, organic components were extracted from the resulting solution four times by using chloroform in portions of 200 ml. From the resulting mixture, the chloroform was removed under vacuum to obtain a solid. The solid was washed with a 10% aqueous solution of $NaHCO_3$ to obtain a mixture of various nitro-compounds. The mixture was dissolved in acetonitrile and was analyzed by high performance liquid chromatography. As a result, it was confirmed that dinitrosotetraacetylhexaazaisowurtzitane was produced as a major component in a 40 percent yield.

Further, the structure of the component was analyzed in the same manner as described in Example 53 and it was found that dinitrosotetraacetylhexaazaisowurtzitane was produced.

Example 64

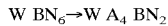
$W\ BN_6 \rightarrow W\ A_4\ BN_2$

In the above formula, A is an acetyl group, BN is a benzyl group and W is a hexavalent hexaazaisowurtzitane residue represented by formula (V).

To a 300 ml autoclave, 1.89 gram of hexabenzylhexaazaisowurtzitane, 1.70 gram of a 10% Pd-C, 5.0 grams of N-acetoxy succinimide, 160 ml of ethylbenzene and 3.24 grams of acetic anhydride were added together with a stirring bar. The atmosphere in the autoclave was replaced by hydrogen gas and the internal pressure was then raised to 5 MPa by further injection of hydrogen gas under pressure. The resulting mixture was reacted for 20 hours while agitating with a magnetic stirrer. After reaction, the resulting reaction solution was taken out from the autoclave and was filtrated through a paper filter to remove Pd-C. The solid on the paper filter was rinsed with 200 ml of chloroform to recover the residual reaction product. The resulting filtrate was mixed with the resulting chloroform solution. The mixture was subjected to solvent evaporation to obtain a solid, which was dissolved in 200 ml of chloroform. To the resulting solution, 200 ml of 28% aqueous ammonia water were added and the resulting mixture was vigorously agitated for 30 minutes. By this operation, N-acetoxy succinimide was separated from the resulting organic phase. The chloroform was then evaporated from the organic phase to obtain 1.39 gram of a white solid. The solid was recrystallized from an ethylbenzene solution to obtain 1.20 gram of a white solid in a 87 percent yield. The solid was analyzed by FD-mass spectrum, $^1$HNMR, $^{13}$CNMR and $^{13}$C—$^1$H COSY and it was confirmed that the solid was tetraacetyldibenzylhexaazaisowurtzitane. Results of the above-mentioned analysis are as follows.

The FD mass spectrum of the above solid had a peak at 517 $(M+H)^+$.

The $^1$H-NMR spectrum of the solid (solvent: $CDCl_3$, TMS: standard reference compound δ: dimensionless quantity of chemical shift in ppm) showed peaks respectively at 1.94 (s, 6H, $COCH_3$), 2.15 (s, 6H, $COCH_3$), 4.06 (d, 2H, $CH_2$), 4.29 (d, 2H, $CH_2$), 5.09 (d, 2H, CH), 5.70 (d, 2H, CH), 6.42 (s, 2H, CH and 7.3–7.5 (m, 10H, Ph), by which 4 acetyl groups, 2 benzyl groups and 6 methine groups of the W skeleton were confirmed.

The $^{13}$C-NMR spectrum of the solid (solvent: $CDCl_3$, TMS: standard reference compound δ: dimensionless quantity of chemical shift in ppm) indicated peaks respectively at 20.737 ($CH_3$), 22.111 ($CH_3$), 56.428 ($CH_2$), 69.679 (CH), 70.592 (CH), 128.056 (Ph), 128.673 (Ph), 128.928 (Ph), 136.742 (Ph) and 168.263 (CO), by which acetyl groups, phenyl groups and methylene groups of benzyl groups and methine groups of the W skeleton were confirmed.

According to $^1$H—$^{13}$C COSY, $^{13}$C linked to $^1$H was identified.

Example 65

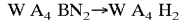
$W\ A_4\ BN_2 \rightarrow W\ A_4\ H_2$

In the above formula, A is an acetyl group, BN is a benzyl group, H is a hydrogen atom and W is a hexavalent hexaazaisowurtzitane residue represented by formula (V).

To a 300 ml autoclave, 3.67 grams of tetraacetyldibenzylhexaazaisowurtzitane, 1.60 gram of $Pd(OAc)_2$ and 150 of acetic acid were added together with a stirring bar. The atmosphere in the autoclave was substituted with nitrogen gas and hydrogen gas was then injected into the autoclave so as to raise the internal pressure to 0.5 MPa. The resulting mixture was reacted for 15 hours while agitating with a magnetic stirrer and was taken out from the autoclave. The mixture was filtrated for removal of the $Pd(OAc)_2$. The resulting solution was subjected to solvent evaporation under vacuum to obtain a solid. The solid was washed with 100 ml of ethyl acetate to obtain 2.33 grams of tetraacetylhexaazaisowurtzitane as a white solid in 99 percent yield. Results of the analysis of the solid are as follows.

The $^1$H-NMR spectrum of the solid (solvent: $D_2O$, TMS: standard reference compound and δ: dimensionless quantity of chemical shift in ppm) showed peaks respectively at 1.98 (s, 6H, $COCH_3$), 2.00 (s, 6H, $CH_3$), 5.29 (br, 2H, CH), 5.50 (br, 2H, CH), 6.35 (m, 2H, CH), by which 4 acetyl groups and methine groups of the W skeleton were confirmed.

As a result of IR absorption spectroscopy of the solid, there were confirmed two absorptions in the region of 3,300–3,400 $cm^{-1}$ ascribed to the stretching vibration of secondary amines (N—H groups) and an absorption at 1,660 $cm^{-1}$ ascribed to the stretching vibration of carbonyl groups (C=O) of acetyl groups, by which it was confirmed that acetyl and N—H groups are present in the W skeleton.

Industrial Applicability

The hexaazaisowurtzitane derivatives of the present invention are useful as precursors of hexanitrohexaazaisowurtzitane which is a high performance explosive.

What is claimed is:

1. A process for preparing a hexanitrohexaazaisowurtzitane represented by the following formula (VI):

$$W N_6 \qquad (VI)$$

wherein N is a nitro group and W is a hexavalent hexaazaisowurtzitane residue, by nitrating with a nitrating agent any one of hexaazaisowurtzitane derivatives represented by the following general formulae (I), (III) and (IV):

$$W A_n N_{(6-n)} \qquad (I)$$

wherein n is an integer of 4 or 5, A is an acyl group having 1–10 carbon atoms with each acyl group being the same as or different from one or more of the others, N is a nitro group and W is a hexavalent hexaazaisowurtzitane residue, $$W A_n NS_{(6-n)} \qquad (III)$$

wherein n is an integer of 4 or 5, A is an acyl group having 1–10 carbon atoms with each acyl group being the same as or different from one or more of the others, NS is a nitroso group and W is a hexavalent hexaazaisowurtzitane residue, and $$W A_m H_{(6-m)} \qquad (IV)$$

wherein m is an integer of 4–6, A is an acyl group having 1–10 carbon atoms with each acyl group being the same as or different from one or more of the others, H is a hydrogen atom and W is a hexavalent hexaazaisowurtzitane residue.

2. A process according to claim 1, wherein the nitrating agent comprises nitric acid and a nitration accelerator.

3. A process according to claim 1, wherein the nitration accelerator is a strong Brønsted acid.

4. A process according to claim 3, wherein the strong Brønsted acid has an acidity equivalent to or stronger than the acidity of trifluoroacetic acid.

5. A process according to claim 3, wherein the strong Brønsted acid is trifluoroacetic acid or sulfuric acid.

6. A process according to claim 3, wherein the strong Brønsted acid is a perfluoroalkylsulfonylimide represented by the following general formula (IX):

$$Rf SO_2 N H SO_2 Rf' \qquad (IX)$$

wherein Rf and Rf' are perfluoroalkyl groups having 1–8 carbon atoms, S is a sulfur atom, O is an oxygen atom, N is a nitrogen atom and H is a hydrogen atom.

7. A process according to claim 2, wherein the nitration accelerator is a carboxylic anhydride.

8. A process according to claim 7, wherein the carboxylic anhydride is trifluoroacetic anhydride.

9. A process according to claim 2, wherein the nitration accelerator is diphosphorus pentoxide or sulfur trioxide.

10. A process according to claim 2, wherein the nitration accelerator is a Lewis acid.

11. A process according to claim 10, wherein the Lewis acid is a rare earth salt of a perfluoroalkylsulfonic acid which is represented by the following general formula (X):

$$M(Rf SO_3)_3 \qquad (X)$$

wherein Rf is a perfluoroalkyl group having 1–8 carbon atoms, S is a sulfur atom, C is an oxygen atom and M is a rare earth element.

12. A process according to claim 10, wherein the Lewis acid is a rare earth salt of a perfluoroalkylsulfonylimide which is represented by the following general formula (XI):

$$M(Rf SO_2 N SO_2 Rf')_3 \qquad (XI)$$

wherein Rf and Rf' are perfluoroalkyl groups having 1–8 carbon atoms, S is a sulfur atom, O is an oxygen atom, N is a nitrogen atom and M is a rare earth element.

13. A process according to claim 2, wherein the nitration accelerator is a strong-acidic solid catalyst.

14. A process according to claim 13, wherein the strong-acidic solid catalyst is a Lewis acid.

15. A process according to claim 13, wherein the strong-acidic solid catalyst is a strong Brønsted acid.

16. A process according to claim 15, wherein the strong Brønsted acid is a polymer having sulfone groups.

17. A process according to claim 15, wherein the strong Brønsted acid is a zeolite.

* * * * *

UNITED STATES PATENT AND TRADEMARK OFFICE
CERTIFICATE OF CORRECTION

PATENT NO.    : 6,297,372 B1
DATED         : October 2, 2001
INVENTOR(S)   : Shuji Kawabe et al.

It is certified that error appears in the above-identified patent and that said Letters Patent is hereby corrected as shown below:

<u>Title page,</u>
Item [57], ABSTRACT,
First line after formula (IV), "N" should read -- m --.
Third line before formula (VI), "and process" should read -- and a process --.

<u>Column 35,</u>
Line 33, "claim 1" should read -- claim 2 --.

Signed and Sealed this

Third Day of September, 2002

*Attest:*

*Attesting Officer*

JAMES E. ROGAN
*Director of the United States Patent and Trademark Office*